US007015246B2

(12) United States Patent
Schmeck et al.

(10) Patent No.: US 7,015,246 B2
(45) Date of Patent: Mar. 21, 2006

(54) BENZOFURAN DERIVATIVES

(75) Inventors: Carsten Schmeck, Wuppertal (DE); Ulrich Müller, Wuppertal (DE); Gunter Schmidt, Wuppertal (DE); Josef Pernerstorfer, Wuppertal (DE); Hilmar Bischoff, Wuppertal (DE); Axel Kretschmer, Wuppertal (DE); Verena Vöhringer, Wuppertal (DE); Christiane Faeste, Oslo (NO); Helmut Haning, Wuppertal (DE); Markus Hauswald, Köln (DE); Delf Schmidt, Wuppertal (DE); Martin Zoche, Aach (DE); Heiner Apeler, Wuppertal (DE); Willi Jonghaus, Wuppertal (DE); Peter Reinemer, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 22 days.

(21) Appl. No.: 10/471,444

(22) PCT Filed: Oct. 10, 2002

(86) PCT No.: PCT/EP02/03304

§ 371 (c)(1), (2), (4) Date: Apr. 12, 2004

(87) PCT Pub. No.: WO02/079181

PCT Pub. Date: Oct. 10, 2002

(65) Prior Publication Data

US 2004/0220415 A1 Nov. 4, 2004

(30) Foreign Application Priority Data

Mar. 29, 2001 (DE) ................................ 101 15 408

(51) Int. Cl.
*C07D 307/79* (2006.01)
*A61K 31/343* (2006.01)

(52) U.S. Cl. ........................ 514/469; 549/505; 549/506

(58) Field of Classification Search ................ 549/505, 549/506; 514/469
See application file for complete search history.

(56) References Cited

U.S. PATENT DOCUMENTS 4,435,422 A * 3/1984 Lee et al. .................. 514/469
6,093,838 A * 7/2000 Vasudevan et al. ......... 549/467

FOREIGN PATENT DOCUMENTS

EP 0483772 5/1992
EP 1063235 12/2000

OTHER PUBLICATIONS

Lee, Cheuk-Man, et al., "[(Aminomethyl)aryloxy]acetic Acid Esters . . . Substituted 6,7-dichloro-2,3-dihydrobenzofurans . . . " J. Med. Chem. 1985, 28, 589-594.*

* cited by examiner

*Primary Examiner*—Joseph K. McKane
*Assistant Examiner*—Susannah Lee

(57) ABSTRACT

The invention relates to novel benzofuran derivatives, to processes for preparing them and to their uses in medicaments.

10 Claims, No Drawings

BENZOFURAN DERIVATIVES

This application is the U.S. National Stage of International Application Number PCT/EP02/03304, filed on Oct. 10, 2002, published in German. This application claims priority under 35 U.S.C. §119 to German Application No. 101 15 408.9, filed on Mar. 29, 2001.

The invention relates to novel benzofuran derivatives, to processes for preparing them and to their uses in medicaments.

The object of the invention is to provide novel compounds which have pharmaceutical effects.

It has now been found that compounds of the general formula (I)

(I)

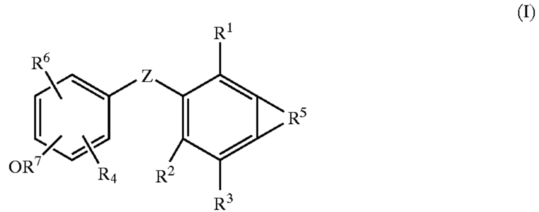

in which

Z is O, S, SO, $SO_2$, $CH_2$, CHF or $CF_2$ or is $NR^8$ in which $R^8$ is hydrogen or $(C_1–C_4)$-alkyl, $R^1$ and $R^2$ are identical or different and are hydrogen, halogen, cyano, $(C_1–C_6)$-alkyl, $CF_3$, $CHF_2$, $CH_2R$, vinyl or $(C_3–C_7)$-cycloalkyl, $R^3$ is hydrogen, halogen, cyano, $(C_1–C_6)$-alkyl or $CF_3$, $R^4$ is hydrogen, hydroxyl, halogen, cyano, nitro, $(C_1–C_4)$-alkyl or the radical of the formula $NR^9R^{10}$, where $R^9$ and $R^{10}$ are identical or different and are in each case hydrogen, phenyl, benzyl, $(C_1–C_6)$-alkyl or $(C_3–C_8)$-cycloalkyl, which, for their part, are optionally substituted, once or more than once, identically or differently, by halogen, hydroxyl, amino, carboxyl, $(C_1–C_4)$-alkoxy, $(C_1–C_4)$-alkoxycarbonyl, $(C_1–C_4)$-alkoxycarbonylamino, $(C_1–C_5)$-alkanoyloxy, a heterocycle or phenyl which is optionally substituted by halogen or hydroxyl, $R^5$ forms, together with the two carbon atoms of the phenyl ring, a saturated or unsaturated furan ring which is optionally substituted, once or twice, identically or differently, $R^6$ is hydrogen, cyano, halogen or a group of the formula $$-M_a-R^{11}$$

in which;

M is a carbonyl group, a sulfonyl group or a methylene group, a is the number 0 or 1 or, in the case where M is a methylene group, is a number 0, 1, 2 or 3, and $R^{11}$ is hydrogen, $OR^{15}$, $NR^{16}R^{17}$, $(C_1–C_{10})$-alkyl, $(C_3–C_8)$-cycloalkyl, $(C_2–C_6)$-alkenyl, $(C_6–C_{10})$-aryl, $(C_6–C_{10})$-arylmethyl or a saturated, partially unsaturated or aromatic 5- to 10-membered heterocycle having up to 4 identical or different heteroatoms from the series N, O and/or S, where the abovementioned radicals are optionally substituted by one, two or three identical or different substituents selected from the group halogen, hydroxyl oxo, cyano, nitro, amino, $NR^{18}R^{19}$, trifluoromethyl, $(C_1–C_6)$-alkyl, $(C_1–C_6)$-alkoxy which is optionally substituted by $R^{20}$, $(C_3–C_8)$-cycloalkyl, $(C_6–C_{10})$-aryl which is, for its part, optionally substituted by halogen, $(C_1–C_4)$-alkyl, $(C_1–C_4)$-alkoxy, trifluoromethyl, nitro or cyano, $—O—C(O)—R^{21}$, $—C(O)—OR^{22}$, $—C(O)—NR^{23}R^{24}$, $—SO_2—NR^{25}R^{26}$, $—NH—C(O)—R^{27}$ and $—NH—C(O)—OR^{28}$, where $R^{15}$ to $R^{28}$ have the meanings given for $R^9$ or $R^{10}$ and, independent of each other, are identical to or different from this substituent, $R^7$ is hydrogen or cation or a group which can be eliminated under physiological conditions with the formation of an OH function, such as, preferably, alkyl or acetyl, and also their pharmaceutically tolerated salts, solvates, hydrates and hydrates of the salts, they exhibit a pharmacological effect and can be used as medicaments or for producing medicament formulations.

Within the context of the invention, heterocycle is preferably a 5- to 10-membered saturated, partially unsaturated or aromatic, where appropriate benzofused heterocycle having up to 4 heteroatoms from the series S, N and/or O, i.e. a heterocycle which can contain one or more double bonds and which is linked by way of a ring carbon atom or a ring nitrogen atom. The following may be mentioned by way of example and as being preferred: tetrahydrofuryl, pyrrolidinyl, pyrrolinyl, piperidinyl, 1,2-dihydropyridinyl, 1,4-dihydropyridinyl, piperazinyl, morpholinyl, azepinyl, 1,4-diazepinyl, furanyl, pyrrolyl, thienyl, thiazolyl, oxazolyl, imidazolyl, triazolyl, tetrazolyl, pyridyl, pyrimidinyl, pyrazinyl, pyridazinyl, pyrimidinonyl and pyridazinonyl.

The following members of this list are preferred: pyridyl, pyrimidinyl, pyridazinyl, pyrimidinonyl, pyridazinonyl and thienyl.

Within the context of the invention, alkyl is a straight-chain or branched alkyl radical preferably having from 1 to 15, from 1 to 12, from 1 to 10, from 1 to 8, from 1 to 6, from 1 to 4 or from 1 to 3 carbon atoms. A straight-chain or branched alkyl radical having from 1 to 3 carbon atoms is preferred. The following may be mentioned by way of example and as being preferred: methyl, ethyl, n-propyl, isopropyl, n-, i-, s- or t-butyl, n-pentyl and n-hexyl.

Within the context of the invention, aryl is an aromatic radical preferably having from 6 to 10 carbon atoms. Phenyl and naphthyl are preferred aryl radicals.

Within the context of the invention, cycloalkyl is a cycloalkyl group preferably having from 3 to 8, from 3 to 7 or from 3 to 6 carbon atoms. The following may be mentioned by way of example and as being preferred: cyclopropyl, cyclobutyl, cyclopentyl, cyclohexyl and cycloheptyl.

Within the context of the invention, alkoxy is preferably a straight-chain or branched alkoxy radical having from 1 to 6, from 1 to 4 or from 1 to 3 carbon atoms. A straight-chain or branched alkoxy radical having from 1 to 3 carbon atoms is preferred. The following may be mentioned by way of example and as being preferred: methoxy, ethoxy, n-propoxy, isopropoxy, t-butoxy, n-pentoxy and n-hexoxy.

Within the context of the invention, alkoxycarbonyl is preferably a straight-chain or branched alkoxy radical having from 1 to 6 or from 1 to 4 carbon atoms which is linked by way of a carbonyl group. A straight-chain or branched alkoxycarbonyl radical having from 1 to 4 carbon atoms is preferred. The following may be mentioned by way of example and as being preferred: methoxycarbonyl, ethoxycarbonyl, n-propoxycarbonyl, isopropoxycarbonyl and t-butoxycarbonyl.

Within the context of the invention, alkanoyloxy is preferably a straight-chain or branched alkyl radical having from 1 to 6, from 1 to 5 or from 1 to 3 carbon atoms which carries a doubly bonded oxygen atom in position 1 and, in position 1, is linked by way of another oxygen atom. A straight-chain or branched alkanoyloxy radical having from 1 to 3 carbon atoms is preferred. The following may be mentioned by way of example and as being preferred: acetoxy, propionoxy, n-butyroxy, i-butyroxy, pivaloyloxy and n-hexanoyloxy.

Within the context of the invention, monoalkylamino is an amino group having a straight-chain or branched alkyl substituent which preferably possesses from 1 to 6, from 1 to 4 or from 1 to 2 carbon atoms. A straight-chain or branched monoalkylamino radical having from 1 to 4 carbon atoms is preferred. The following may be mentioned by way of example and as being preferred: methylamino, ethylamino, n-propylamino, isopropylamino, t-butylamino, n-pentylamino and n-hexylamino.

Within the context of the invention, dialkylamino is an amino group having two identical or different straight-chain or branched alkyl substituents which preferably in each case possess from 1 to 6, from 1 to 4 or from 1 to 2 carbon atoms. Straight-chain or branched dialkylamino radicals having in each case from 1 to 4 carbon atoms are preferred. The following may be mentioned by way of example and as being preferred: N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Within the context of the invention, monoacylamino is an amino group having a straight-chain or branched alkanoyl substituent which preferably possesses from 1 to 6, from 1 to 4 or from 1 to 2 carbon atoms and is linked by way of the carbonylgroup. A monoacylamino radical having from 1 to 2 carbon atoms is preferred. The following may be mentioned by way of example and as being preferred: formamido, acetamido, propionamido, n-Butyramido and pivaloylamido.

Within the context of the invention, alkoxycarbonylamino is an amino group having a straight-chain or branched alkoxycarbonyl substitutent which preferably possesses from 1 to 6 or from 1 to 4 carbon atoms in the alkoxy radical and is linked by way of the carbonyl group. An alkoxycarbonylamino radical having from 1 to 4 carbon atoms is preferred. The following may be mentioned by way of example and as being preferred: methoxycarbonyl-amino, ethoxycarbonylamino, n-propoxycarbonylamino and t-butoxycarbonylamino.

Within the context of the invention, halogen includes fluorine, chlorine, bromine and iodine. Fluorine, chlorine or bromine is preferred.

Depending on the substitution pattern, the compounds according to the invention can exist in stereoisomeric forms which either relate to each other as image and mirror image (enantiomers) or which do not relate to each other as image and mirror image (diastereomers). The invention relates to both the enantiomers and the diastereomers and to their respective mixtures. The racemic forms, just like the diastereomers, can be separated, in a known manner, into the stereoisomerically homogeneous constituents.

In addition, certain compounds can be present in tautomeric forms. This is known to the skilled person, and such compounds also come within the scope of the invention.

The compounds according to the invention can also be present as salts. Within the context of the invention, preference is given to physiologically harmless salts.

Physiologically harmless salts can be salts of the compounds according to the invention with inorganic or organic acids. Preference is given to salts with inorganic acids, such as hydrochloric acid, hydrobromic acid, phosphoric acid or sulfuric acid, or salts with organic carboxylic or sulfonic acids, such as acetic acid, propionic acid, maleic acid, fumaric acid, malic acid, citric acid, tartaric acid, lactic acid or benzoic acid or methanesulfonic acid, ethanesulfonic acid, benzenesulfonic acid, toluenesulfonic acid or naphthalenedisulfonic acid.

Physiologically harmless salts can also be salts of the compounds according to the invention with bases, for example metal salts or ammonium salts. Preferred examples are alkali metal salts (e.g. sodium salts or potassium salts), alkaline earth metal salts (e.g. magnesium salts or calcium salts), and also ammonium salts which are derived from ammonia or organic amines, such as ethylamine, diethylamine, triethylamine, ethyldiisopropylamine, monoethanolamine, diethanolamine, triethanolamine, dicyclohexylamine, dimethylaminoethanol, dibenzylamine, N-methylmorpholine, dihydroabietylamine, 1-ephenaminme, methylpiperidine, arginine, lysine, ethylenediamine or 2-phenylethylamine.

The compounds according to the invention can also be present in the form of their solvates, in particular in the form of their hydrates.

Preference is given to compounds of the general formula (I), in which

Z is O, S or $CH_2$, $R^1$ and $R^2$ are identical or different and are halogen, fluorine, chlorine, bromine, $(C_1–C_4)$-alkyl, $CF_3$, $CHF_2$, $CH_2F$, vinyl or $(C_3–C_5)$-cycloalkyl, $R^3$ is hydrogen, fluorine, chlorine, bromine, $(C_1–C_4)$-alkyl or $CF_3$, $R^4$ is hydrogen, halogen or $(C_1–C_4)$-alkyl, $R^5$ forms, together with the two carbon atoms of the phenyl ring, a saturated or unsaturated furan ring which is optionally substituted, once or twice, identically or differently, $R^6$ is hydrogen, cyano, halogen or a group of the formula $$-M_a-R^{11}$$

in which

M is a carbonyl group, a sulfonyl group or a methylene group, a is the number 0 or 1, and $R^{11}$ is hydrogen, hydroxyl, $(C_1–C_6)$-alkoxy, $NR^{16}R^{17}$, $(C_1–C_{10})$-alkyl, $(C_3–C_7)$-cycloalkyl, $(C_2–C_4)$-alkenyl, naphthyl, phenyl, benzyl, pyridyl, pyridazinyl or pyridazinonyl, where the abovementioned radicals are optionally substituted by one, two or three identical or different substituents selected from the group halogen, hydroxyl, cyano, nitro, amino, $NR^{18}R^{19}$, trifluoromethyl, $(C_1–C_4)$-alkyl, $(C_1–C_4)$-alkoxy, $(C_3–C_7)$-cycloalkyl, phenyl which is, for its part, optionally substituted by halogen, $(C_1–C_4)$-alkyl, $(C_1–C_4)$-alkoxy, trifluoromethyl, nitro or cyano, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{16}$, $R^{17}$, $R^{18}$, $R^{19}$, $R^{21}$, $R^{22}$, $R^{23}$, $R^{24}$, $R^{25}$, $R^{26}$, $R^{27}$ and $R^{28}$ are identical or different and are in each case hydrogen, phenyl, benzyl, $(C_1–C_6)$-alkyl or $(C_3–C_6)$-cycloalkyl which, for their part, are optionally substituted, once or more than once, identically or differently, by halogen, hydroxyl, amino, carboxyl, $(C_1–C_4)$-alkoxy, $(C_1–C_4)$-alkoxycarbonyl, $(C_1–C_4)$-alkoxycarbonyl-amino, $(C_1–C_5)$-alkanoyloxy, a heterocycle or phenyl which is optionally substituted by halogen or hydroxyl, $R^7$ is hydrogen, and their pharmaceutically tolerated salts, solvates and hydrates of the salts.

Particular preference is given to compounds of general formula (I), in which

Z is O or $CH_2$, $R^1$ and $R^2$ are identical or different and are hydrogen, fluorine, chlorine, bromine, methyl, ethyl, n-, i- or s-propyl, n-, i-, s- or t-butyl, $CF_3$, $CHF_2$, $CH_2F$, vinyl or $(C_3–C_5)$-cycloalkyl, $R^3$ is hydrogen or methyl, $R^4$ is methyl, fluorine, chlorine or, in particular, hydrogen, $R^5$ forms, together with the two carbon atoms of the phenyl ring, a saturated or unsaturated furan ring which is optionally substituted, once or twice, identically or differently, $R^6$ is hydrogen, cyano, halogen or a group of the formula $-M_a-R^{11}$ in which M is a carbonyl group or a methylene group, a is the number 0 or 1, and $R^{11}$ is hydrogen, hydroxyl, $(C_1–C_4)$-alkyl, $(C_1–C_4)$-alkoxy, $NR^{18}R^{19}$, —CH(OH)—$R^{29}$, $(C_3–C_7)$-cycloalkyl, phenyl, benzyl, pyridyl, pyridazinyl or pyridazinonyl, where the abovementioned radicals are optionally substituted by one or two identical or different substituents selected from the group fluorine, chlorine, bromine, hydroxyl, cyano, nitro, amino, $NR^{18}R^{19}$, trifluoromethyl, $(C_1–C_4)$-alkyl, $(C_1–C_4)$-alkoxy, $(C_3–C_7)$-cycloalkyl, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{18}$, $R^{19}$, $R^{21}$, $R^{22}$, $R^{23}$, $R^{24}$, $R^{25}$, $R^{26}$, $R^{27}$, $R^{28}$ and $R^{29}$ are identical or different and are in each case hydrogen, phenyl, benzyl, $(C_1–C_4)$-alkyl or $(C_3–C_6)$-cycloalkyl which, for their part, are optionally substituted, once or twice, identically or differently, by fluorine, chlorine, hydroxyl, amino, carboxyl, $(C_1–C_4)$-alkoxy, $(C_1–C_4)$-alkoxycarbonyl, $(C_1–C_4)$-alkoxycarbonyl-amino, $(C_1–C_5)$-alkanoyloxy, a heterocycle or phenyl which is optionally substituted by fluorine, chlorine or hydroxyl, $R^7$ is hydrogen, and also their pharmaceutically tolerated salts, solvates and hydrates and hydrates of the salts.

Very particular preference is given to compounds of the general formula (I), in which Z is O, $R^1$ and $R^2$ are identical or different and are hydrogen, bromine, chlorine, $CF_3$ or methyl with the proviso that at least one constituent is not hydrogen, $R^3$ is hydrogen or methyl, $R^4$ is hydrogen, $R^5$ forms, together with the two carbon atoms of the phenyl ring, a saturated or unsaturated furan ring which is optionally substituted, once or twice, identically or differently, $R^6$ is hydrogen, methyl, ethyl n- or i-propyl, n-, i-, s- or t-butyl, or is a carbonyl group or a group —CH(OH) which is substituted by phenyl which is optionally substituted by fluorine, chlorine, cyano, nitro, trifluoromethyl, methyl, methoxy, carboxyl or methoxycarbonyl, $R^7$ is hydrogen, and also their pharmaceutically tolerated salts, solvates and hydrates and hydrates of the salts.

Compounds of the general formula (I) are of particular importance in which $R^5$ forms, together with the two carbon atoms of the phenyl ring, a group (Ib), (Ic) or (Id)

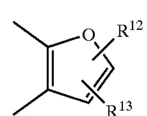

(Ib)

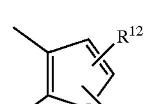

(Ic)

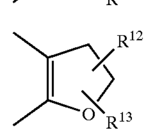

(Id)

in which $R^{12}$ and $R^{13}$ are identical or different and are hydrogen, $(C_1–C_6)$alkyl, $(C_1–C_6)$-alkoxy, halogen, or are a group of the formula —$NR^{30}R^{31}$, in which $R^{30}$ and $R^{31}$ are identical or different and are hydrogen, $(C_1–C_6)$alkyl or $(C_3–C_8)$cycloalkyl which are optionally substituted by amino or $(C_1–C_6)$alkoxy, or are a group of the formula $-A-(CH_2)_n—C(O)—R^{32}$ in which A is a bond, O, S or C(O), or is a straight-chain or branched alkylene group having from 1 to 6 carbon atoms which is optionally substituted by halogen, hydroxyl and/or amino, or is $NR^{33}$, in which $R^{33}$ is hydrogen, $(C_1–C_6)$alkyl or $(C_3–C_8)$cycloalkyl which are optionally substituted by amino or $(C_1–C_6)$ alkoxy, n is a number from 0 to 3

$R^{32}$ is hydroxyl, halogen or $(C_1–C_6)$alkyl or is a group —$NR^{30}R^{31}$ or is a group —$OR^{34}$ in which $R^{30}$, $R^{31}$ and $R^{34}$ have the abovementioned meaning of $R^{30}$ and $R^{31}$ and can be identical to or different from these latter.

Preference is given to compounds of the formula (I) in which $R^5$ forms, together with the two carbon atoms of the phenyl ring, a group (Ib), (Ic) or (Id)

in which $R^{12}$ and $R^{13}$ are identical or different and are hydrogen, $(C_1–C_4)$alkyl, $(C_1–C_4)$-alkoxy, halogen, or a group of the formula —$NR^{30}R^{31}$ in which $R^{30}$ and $R^{31}$ are identical or different and are hydrogen, $(C_1–C_4)$alkyl or $(C_3–C_7)$cycloalkyl which are optionally substituted by amino or $(C_1–C_4)$alkoxy, or $R^{12}$ and $R^{13}$ are identical or different and are a group of the formula $-A-(CH_2)_n—C(O)—R^{32}$ in which A is a bond or O, S, $NR^{33}$ or, in particular, is a straight-chain or branched alkylene group having from 1 to 4 carbon atoms which is optionally substituted by fluorine, chlorine, bromine, hydroxyl and/or amino, or is C(O), in which $R^{33}$ is hydrogen, methyl or ethyl, n is a number from 0 or 1

$R^{32}$ is hydroxyl, halogen or $(C_1–C_4)$alkyl or is a group —$NR^{30}R^{31}$ or is a group —$OR^{34}$, in which $R^{30}$, $R^{31}$ and $R^{34}$ are identical or different and are hydrogen $(C_1–C_4)$alkyl or $(C_3–C_7)$cycloalkyl which are optionally substituted by amino or $(C_1–C_4)$alkoxy.

Particular preference is given to compounds of formula (I) in which $R^5$ forms, together with the two carbon atoms of the phenyl ring, a group (Ib'), (Ic') or (Id')

(Ib')

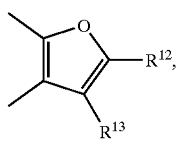

(Ic')

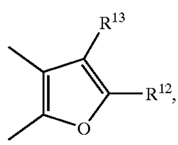

(Id')

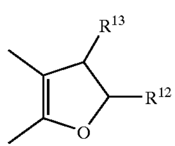

in which $R^2$ is methyl, ethyl, n-, i- or s-propyl, n-, i-, s- or t-butyl or is the group of the formula

-A-C(O)—$R^{32}$ in which

A is a methylene group which is optionally substituted by fluorine, chlorine, bromine, hydroxyl or amino or is, in particular, unsaturated, $R^{32}$ is hydroxyl, chlorine, methyl, ethyl, n-, i- or s-propyl, n-, i-, s- or t-butyl, methoxy, ethoxy, n-, i- or s-propoxy, n-, i-, s- or t-butoxy or $(C_1–C_4)$alkyl or is a group —$NR^{30}R^{31}$ or is a group —$OR^{34}$, in which $R^{30}$, $R^{31}$ and $R^{34}$ are identical or different and are hydrogen, $(C_1–C_4)$alkyl or $(C_3–C_7)$cycloalkyl which are optionally substituted by amino or $(C_1–C_4)$ alkoxy, and $R^{13}$ has the abovementioned meaning of $R^{12}$ and can be identical to or different from the latter or is, in particular, hydrogen.

The above-listed general radical definitions, or those specified in preference ranges, apply both to the end products of the formula (I) and, correspondingly, to the starting compounds and/or intermediates which are in each case required for the preparation.

The radical definitions which are specified in detail in the respective combinations or preferred combinations of radicals are also replaced as desired, independently of the radical combinations which are specified at the time, by radical definitions of other combinations.

Particular preference is given to compounds of the formula (I) in which Z is oxygen.

Particular preference is given to compounds of the formula (I) in which $R^3$ is hydrogen or methyl.

Particular preference is given to compounds of the formula (I) in which $R^4$ is hydrogen.

Particular preference is given to compounds of formula (I) in which $R^1$ and $R^2$ are both chlorine, trifluoromethyl, ethyl, cyclopropyl and are, in particular, methyl or bromine.

Very particular preference is given to compounds of the formula (Ia)

(Ia)

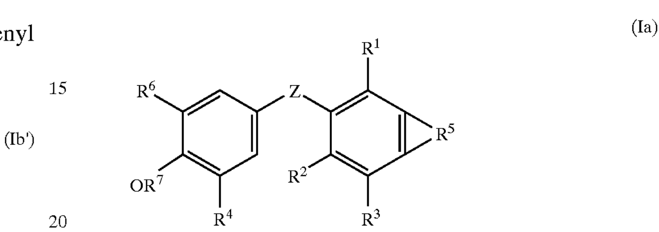

The following individual compounds may be mentioned by way of example and as being preferred:

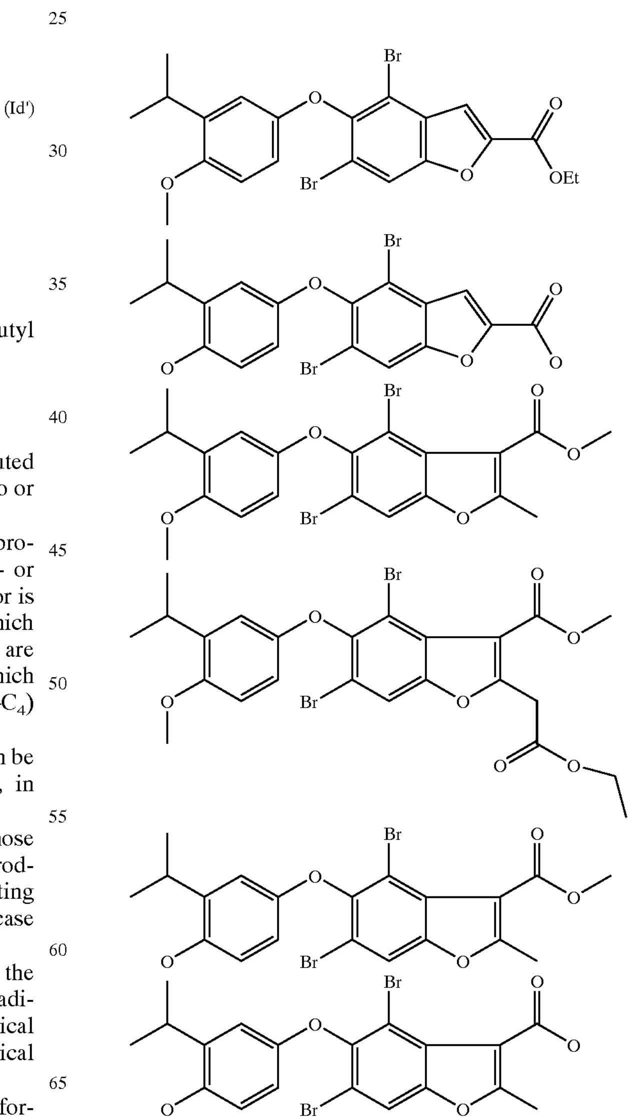

-continued
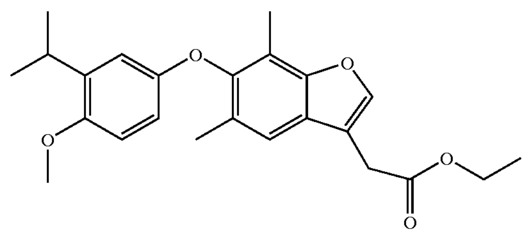
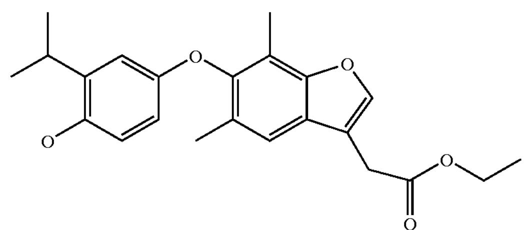
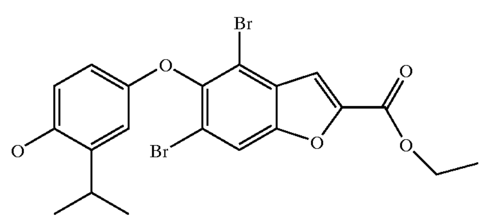
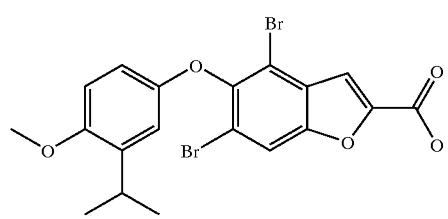
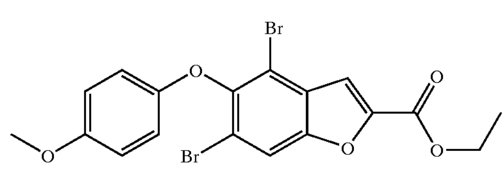
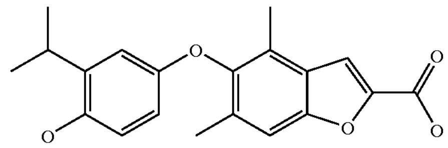
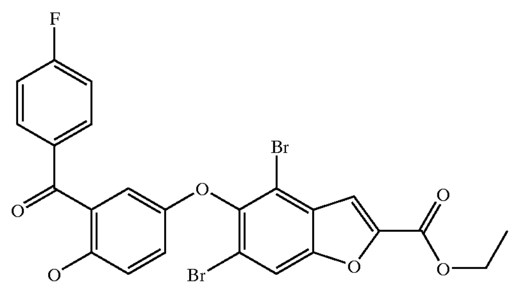
-continued
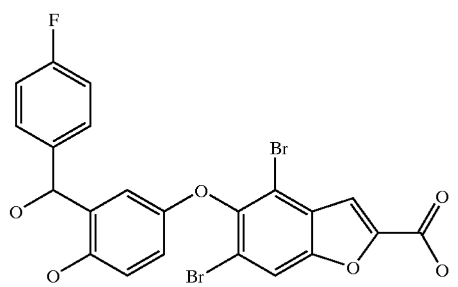
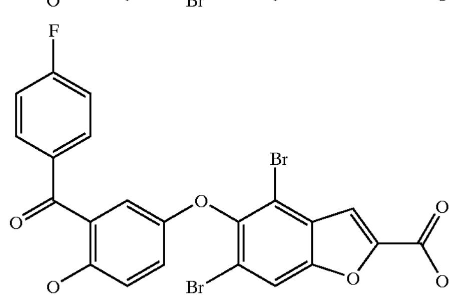
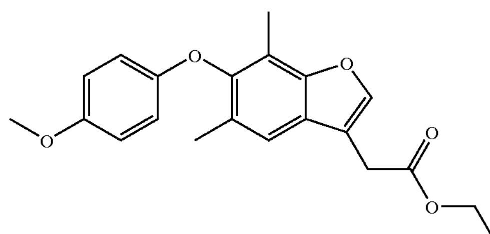
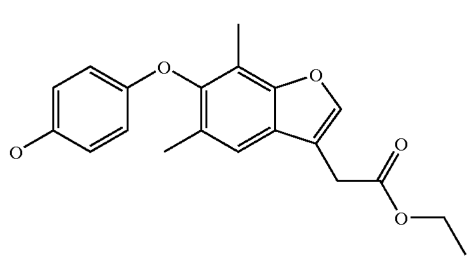
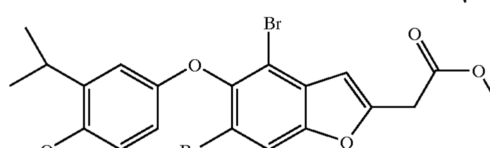
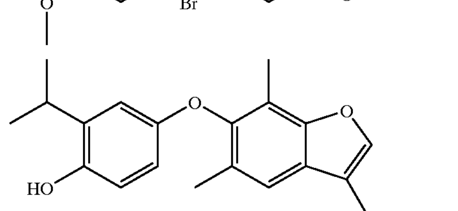
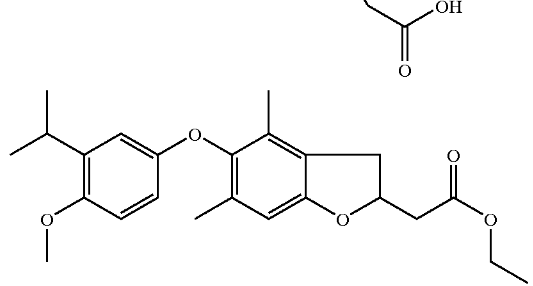

-continued

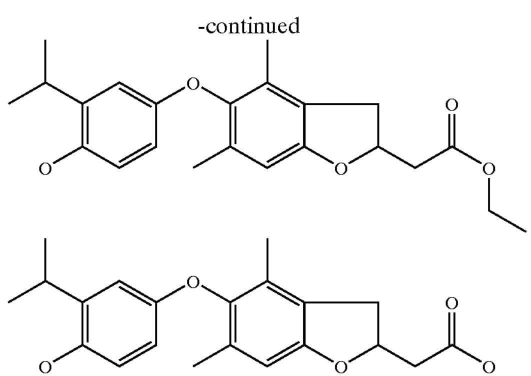

The compounds according to the invention of the general formula (I) can be prepared by reacting reactive benzofuran derivatives of the general formula (II) with reactive phenyl derivatives of the general formula (III)

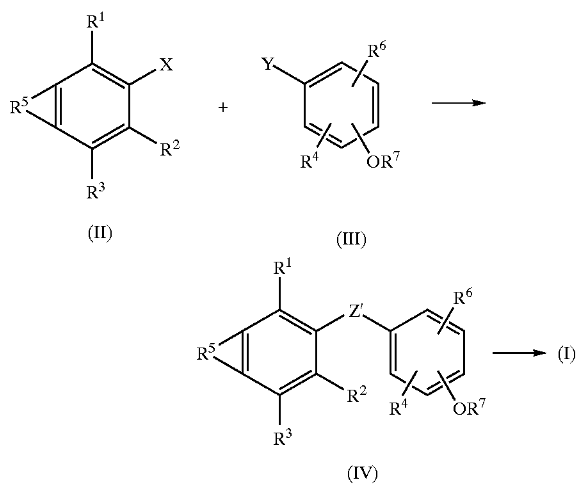

where the substituents $R^1$, $R^2$, $R^4$, $R^5$, $R^6$ and $R^7$ have the abovementioned meanings, and X and Y are in each case groups of opposing reactivity, with it being possible, for example, for X to be an electrophilic radical which reacts with a nucleophilic Y substituent and vice versa, Z' has the meaning given for Z or is

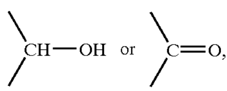

where appropriate in the presence of inert solvents and catalysts and where appropriate with isolation of the intermediates of the general formula (IV), or directly to give compounds of the formula (I).

Catalysts which may be mentioned by way of example are coupling catalysts such as Pd compounds, Rh compounds and/or Cu compounds.

The following may be mentioned by way of example for the reactive groups X and/or Y: halogen, hydroxyl, $CH_2Br$, mercapto, amino, CHO, Li or magnesium derivatives, tin derivatives or boron derivatives.

The benzofuran derivatives of the general formula (II) which can be used in accordance with the invention are either known or can be prepared using known methods [compare, e.g., Ozaki et al., Heterocycles 51, 727–731 (1999); Harvey et al., J. Chem. Soc., 473 (1959); Quadbeck et al., Hoppe-Seyler's Z. Physiolog. Chem. 297, 229 (1954); Chen et al., J. Org. Chem. 59, 3738 (1994); Synthesis, 480 (1988); J. prakt. Chem. 340 608 (1998), Kuhn; Staab et al; Chem. Ber.; 87; 1956; 266, 270; Grinev; Jotova; Chem. Heterocycl. Compd. (Engl. Transl.); 11; 1975; 401].

The phenyl derivatives of the general formula (III) are likewise either known or can be prepared using known methods [compare, e.g., van de Bunt, Recl. Trav. Chim. Pays-Bas 48, 131 (1929); Valkanas, J. Chem. Soc., 5554 (1963)].

In general, the reaction of the starting compounds (II) with (III) proceeds under standard pressure. However, it can also be carried out under elevated or reduced pressure.

The reaction can be carried out in a temperature range of from −100° C. to 200° C., preferably between −78° C. and 150° C., in the presence of inert solvents. Inert solvents which may be mentioned as being preferred are: dimethylsulfoxide (DMSO), dimethylformamide (DMF), tetrahydrofuran (THF), diethyl ether, dichloroethane, dichloromethane, etc.

Depending on the specific substituent pattern, it is also possible, in the reaction of (II) and (III), to form intermediates of the formula (IV) in which, for example, the substituent $R^{3'}$ is a nitro group, aldehyde group, cyano group, carboxyl group or alkoxycarbonyl group, or Z' is a CHOH group or C(O) group, which are then, with or without isolation of these intermediates, subjected to further reaction, using customary methods, to give compounds of the formula (I).

By way of example, the process according to the invention can be explained by means of the following formula schemes:

Process variant (A)

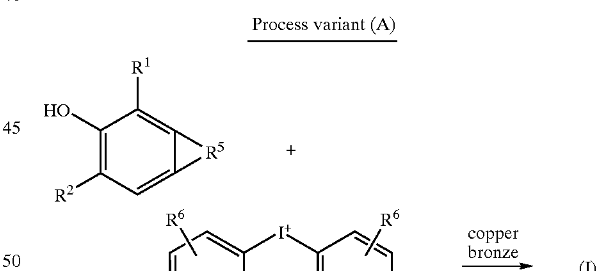

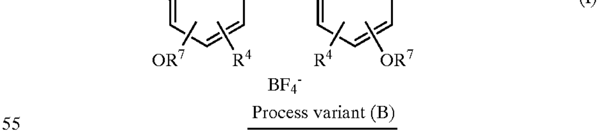

Process variant (B)

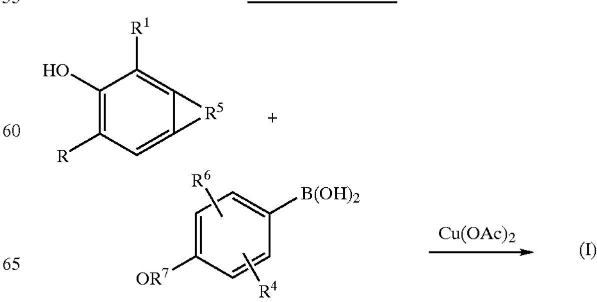

-continued

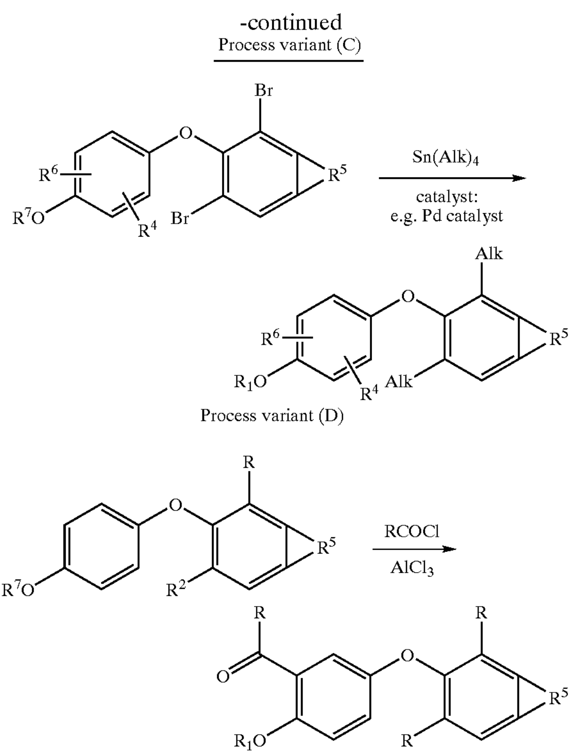

Depending on the meaning of the substituents $R^1$, $R^2$, $R^4$, $R^5$, $R^6$, $R^7$ and $R^8$, it may be appropriate or necessary to vary them within the given range of meanings at individual process steps.

In the present application, protective groups (PG) are understood as meaning those groups in starting compounds, intermediates and/or end products which protect the functional groups which are present, such as carboxyl, amino, mercapto or hydroxyl groups, and which are customary in preparative organic chemistry. The groups which are protected in this way can then be readily converted, under known conditions, into free functional groups.

The compounds according to the invention of the formula (I) exhibit a surprising and valuable pharmacological spectrum of activity and can therefore be used as versatile medicaments. In particular, they can be used in the case of all indications which can be treated with natural thyroid hormones, such as, by way of example and preferably, depression, goiter or thyroid cancer. The compounds according to the invention of the formula (I) are preferably used for treating arteriosclerosis, hypercholesterolemia and dyslipidemia. In addition to this, they can also be used to treat obesity and cardiac insufficiency and to achieve a postprandial reduction in triglycerides.

The compounds are also suitable for treating certain respiratory tract diseases, in particular lung emphysema and for the medicinal promotion of lung maturation.

In addition, the compounds are suitable for treating Alzheimer's disease.

The compounds are also suitable for treating osteoporosis, cardiac rhythm disturbances, hypothyroidisms and skin diseases.

In addition, the compounds can also be used for promoting and regenerating hair growth and for treating diabetes.

The active compounds according to the invention open up the possibility of using another alternative treatment and enrich pharmacy. The compounds according to the invention exhibit a spectrum of activity which is superior to that of the known and previously employed thyroid hormone preparations. The compounds according to the invention are preferably characterized by a high degree of specificity, by being well tolerated and by having few side-effects, particularly in the cardiovascular area.

The activity of the compounds according to the invention can be tested, for example, in vitro using the T3 Promoter Assay Cell test, which is described below:

The test is carried out using a stably transfected human HepG2 hepatocarcinoma cell which expresses a luciferase gene under the control of a thyroid hormone-regulated promoter. The vector which is used for the transfection carries a minimal thymidine kinase promoter, containing a thyroid hormone-responsive element (TRE) which consists of two inverted palindromes of in each case 12 bp and an 8 bp spacer, upstream of the luciferase gene.

For the test, the cell cultures are sown, in Eagle's minimal essential medium containing the following additions: glutamine, tricine [N(tris-(hydroxymethyl)-methyl)glycine], sodium pyruvate, non essential amino acids, (L-Ala, L-Asn, L-Asp, L-Pro, L-Ser, L-Glu, Gly), insulin, selenium and transferrin, in 96-well plates. The cultures are grown for 48 hours at 37° C. and under a 10% $CO_2$ atmosphere. After that, serial dilutions of test substance or reference compound (T3, T4) and costimulator retinoic acid are added to the test cultures and the latter are incubated for a further 48 or 72 hours as before. Each substance concentration is tested in four replicates. In order to determine the luciferase which is induced by T3 or other substances, the cells are then lyzed by adding a buffer containing Triton and luciferin (from Promega) and immediately measured luminometrically.

The compounds according to the invention also display surprisingly advantageous properties in the in-vivo test described below:

Description of a test for finding pharmacologically active substances which lower serum cholesterol in mice:

The substances which are to be investigated for their serum cholesterol-lowering effect in vivo are administered orally to male mice having a body weight of between 25 and 35 g. On the day before beginning the experiment, the animals are divided into groups containing the same numbers of animals, as a rule n=7–10. During the entire experiment, drinking water and food are available to the animals ad libitum. The substances are administered orally once a day for 7 days. For this purpose, the test substances are dissolved in a solution composed of solutol HS 15+ethanol+sodium chloride solution (0.9%) in the ratio 1+1+8 or in a solution composed of solutol HS 15+sodium chloride solution (0.9%) in the ratio 2+8. The dissolved substances are administered in a volume of 10 ml/kg of body weight using a probang. Mice which are treated in precisely the same way but which are only given the solvent (10 ml/kg of body weight) without test substance serve as the control group.

Prior to the first administration of substance, blood is withdrawn from each mouse, by puncturing the retroorbital venous complex, for the purpose of determining the serum cholesterol (preliminary value). The test substance is then administered for the first time to the animals using a probang. 24 hours after the last administration of substance (on the 8th day after beginning the treatment), blood is once again withdrawn from each animal, by puncturing the retroorbital venous complex, in order to determine the serum cholesterol. The blood samples are centrifuged and, after the serum has been isolated, the cholesterol is determined photometrically using an EPOS Analyzer 5050 (Eppendorf- Gerätebau, Netheler & Hinz GmbH, Hamburg). The determination is carried out using a commercially available enzyme test (Boehringer Mannheirn, Mannheim).

The effect of the test substances on the serum cholesterol concentration is determined by subtracting the cholesterol value found in the 1st blood sample (preliminary value) from the cholesterol value found in the 2nd blood sample (after treatment). The differences for all the cholesterol values in a group are averaged and compared with the mean of the differences in the control group.

The results are statistically analyzed by Student's t test after the variants have been previously checked for homogeneity.

Substances which lower the serum cholesterol of the treated animals statistically significantly ($p<0.05$) by at least 10%, when compared with the control group, are regarded as being pharmacologically active.

At the end of the experiment, the animals are weighed and, after withdrawing blood, are sacrificed. The hearts are then removed and weighed in order to test for potential cardiovascular side-effects under the influence of the substance. A significant increase in the weight of the heart indicates that there has been an effect on the cardiovascular system. A change in body weight can be invoked as another parameter for the effect of the substance.

NMRI mice, ob,ob mice, Wistar rats or fa,fa Zucker rats can, for example, be used as experimental animals for this test in an analogous manner.

The cholesterol-fed rat animal model [A. Taylor et al., Molecular Pharmacology 52, 542–547 (1997); Z. Stephan et al., Atherosclerosis 126, 53–63 (1996)] is another in-vivo test in which the compounds according to the invention exhibit surprisingly advantageous properties.

The cholesterol-lowering effect of the compounds according to the invention can also be tested in normocholesterolemic dogs by administering the test substances orally for 5–7days.

In order to further investigate potential cardiovascular side-effects occurring under the influence of the substances, it is possible, inter alia, to determine the expression of the "HCN2" ion channel ("hyperpolarization-activated cyclic nucleotide-gated channel") mRNA in mouse or rat. hearts [cf. also; Trost et al., Endocrinology 141 (9), 3057–3064 (2000); Gloss et al., Endocrinology 142 (2), 544–550 (2001); Pachuki et al., Circulation Research 85, 498–503 (1999)]:

HCN2 Assay

The hyperpolarization-activated cyclic nucleotide-gated (HCN2) cation channel mRNA in rat hearts was quantified by means of real-time PCR (TaqMan-PCR; Heid et al., Genome Res. 6 (10), 986–994). To do this, the hearts were first of all dissected out and the total RNA was then isolated using RNaesy columns (from Qiagen), digested with DNase and then transcribed into cDNA (SUPERSCRIPT-II RT cDNA synthesis kit, from Gibco). The HCN2 MRNA was determined on an ABI Prism 7700 instrument (from Applied Biosystems). The sequences of the forward and reverse primers were: 5'-GGGAATCGACTCCGAGGTC-3' and 5'-GATCTTGGTGAAACGCACGA-3', respectively, while that of the fluorescent probe was 5'-6FAM-ACAAGACG-GCCCGTGCACTACGC-TAMRA-3. During the polymerase chain reaction, the fluorescent dye FAM is cleaved off by the 5'-exonuclease activity of the Taq polymerase, thereby giving rise to the previously quenched fluorescent signal. The cycle number at which the fluorescence intensity was 10 standard deviations above the background fluorescence was recorded as being the threshold cycle (CT value). The relative expression of the HCN2 mRNA which was calculated in this way was then normalized to the expression of the ribosomal protein L32.

This assay can also be carried out in an analagous manner using mouse hearts. In this case, the sequences of the forward and reverse primers were 5'-CGAGGTGCTGGAG-GAATACC-3' and 5'-CTAGCCGGTCAATAGCCACAG-3', respectively, while that of the fluorescent probe was 5'-6F All the customary modes of administration are suitable for administering the compounds of the general formula (I), i.e., therefore, oral, parenteral, by inhalation, nasal, sublingual, buccal, rectal or external, for example transdermal, with oral or parenteral being particularly preferred. In the case of parenteral administration, particular mention should be made of intravenous, intramuscular and subcutaneous administration, for example as a subcutaneous depot. Oral administration is very particularly preferred.

In this connection, the active compounds can be administered either alone or in the form of preparations. Suitable preparations for oral administration are, inter alia, tablets, capsules, pellets, sugar-coated tablets, pills, granules, solid or liquid aerosols, syrups, emulsions, suspensions and solutions. In connection with this, the active compound has to be present in a quantity which is such that a therapeutic effect is achieved. In general, the active compound can be present at a concentration of from 0.1 to 100% by weight, in particular from 0.5 to 90% by weight, preferably from 5 to 80% by weight. In particular, the concentration of the active compound should be from 0.5 to 90% by weight, i.e. the active compound should be present in quantities which are sufficient to achieve the specified dosage latitude.

For this purpose, the active compounds can be converted into the customary preparations in a manner known per se. This is effected using inert, nontoxic, pharmaceutically suitable carrier substances, auxiliary substances, solvents, vehicles, emulsifiers and/or dispersants.

The following auxiliary substances may be cited by way of example: water, nontoxic organic solvents such as paraffins, vegetable oils (e.g. sesame oil), alcohols (e.g. ethanol and glycerol), glycols (e.g. polyethylene glycol), solid carrier substances such as natural or synthetic mineral powders (e.g. talc or silicate), sugars (e.g. lactose), emulsifiers, dispersants (e.g. polyvinylpyrrolidone) and lubricants (e.g. magnesium sulfate).

In the case of oral administration, tablets can naturally also contain additives such as sodium citrate together with fillers such as starch, gelatin and the like. Taste improvers or dyes can also be added to aqueous preparations for oral administration.

Doses of from 0.001 to 5 mg/kg, preferably of from 0.001 to 3 mg/kg of body weight are preferably administered every 24 hours in the case of oral administration.

The novel active compounds can be administered either alone or, as required, also in combination with other active compounds, preferably from the group CETP inhibitors, antidiabetics, antioxidants, cytostatic agents, calcium antagonists, hypertensive agents, thyroid hormones, HMG-CoA reductase inhibitors, inhibitors of HMG-CoA reductase gene expression, squalene synthesis inhibitors, ACAT inhibitors, blood flow-promoting agents, platelet aggregation inhibitors, anticoagulants, angiotensin II receptor antagonists, cholesterol absorption inhibitors, MTP inhibitors, fibrates, niacin, anorectics, lipase inhibitors and PPAR agonists.

The following implementation examples are intended to explain the invention by way of example without having any restricting effect on the scope of protection.

| Abbreviations employed: | |
|---|---|
| TLC | Thin layer chromatography |
| DCI | Direct chemical ionization (in MS) |
| DMF | N,N-dimethylformamide |
| DMSO | dimethyl sulfoxide |
| EI | Electron impact ionization (in MS) |
| HPLC | High pressure, high performance liquid chromatography |
| conc. | concentrated |
| MS | Mass spectroscopy |
| NMP | N-methylpyrrolidinone |
| NMR | Nuclear resonance spectroscopy |
| $R_f$ | Retention index (in DC) |
| $R_t$ | Retention time (in HPLC) |
| THF | Tetrahydrofuran |
| aq. | aqueous |
| Decomp. | Decomposition |

EXAMPLES 1. 1,3-Dihydroxy-2,4-dimethylbenzene

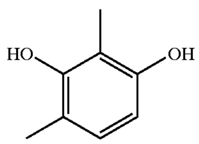

1 g (6.5 mmol) of 2,4-dihydroxy-3-methylbenzaldehyde is hydrogenated, at 3 bar hydrogen pressure for 24 h, with 100 mg of Pd on active charcoal (10%) in 100 ml of methanol and 1 ml of glacial acetic acid. A further 100 mg of Pd on active charcoal (20%) are added and the mixture is hydrogenated at 3 bar hydrogen pressure for 12 h. The catalyst is filtered off, the solvent is removed in vacuo and the residue is purified by chromatography (dichloromethane/acetone). 274 mg (30%) of 1,3-dihydroxy-2,4-dimethylbenzene are obtained.

$^1$H-NMR (200 MHz, $d_6$-DMSO, TMS): 1.96, s, 3H; 2.04, s, 3H; 6.22, d, 1H; 6.63, d, 1H; 7.95, s, 1H; 8.82, s, 1H.

2. 4-(Chloromethyl)-7-hydroxy-6,8-dimethyl-2H-chromen-2-one

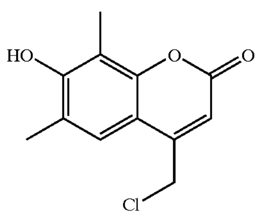

3.3 g (23.8 mmol) of 1,3-Dihydroxy-2,4-dimethylbenzene are stirred overnight at room temperature in 26 ml of conc. sulfuric acid together with 4.72 g (28.7 mmol) of ethyl chloroacetate. The reaction mixture is poured on to 600 ml of ice water and this mixture is extracted 3 times with ethyl acetate; the organic phase is then washed with a saturated solution of NaCl and dried over sodium sulfate. The solvent is removed in vacuo. 4.96 g (87%) of 4-(chloromethyl)-7-hydroxy-6,8-dimethyl-2H-chromen-2-one are obtained.

$^1$H-NMR (300 MHz, DMSO-$d_6$, TMS): 2.22, s, 3H; 2.26, s, 3H; 4.95, s, 2H; 6.41, s, 1H; 7.45, s, 1H.

3. 2-(6-Hydroxy-5,7-dimethyl-1-benzofuran-3-yl)acetic acid

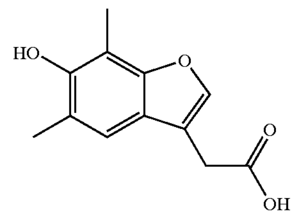

4.8 g (20.1 mmol) of 4-(Chloromethyl)-7-hydroxy-6,8-dimethyl-2H-chromen-2-one are heated at reflux for 3 h in 11 of 0.2 N NaOH. The reaction solution is adjusted to pH 3 with HCl and extracted 4 times with ethyl acetate. The combined organic phases are washed with a saturated solution of NaCl, dried over sodium sulfate and concentrated. 3.3 g (75%) of 2-(6-hydroxy-5,7-dimethyl-1-benzofuran-3-yl) acetic acid are obtained.

$^1$H-NMR (300 MHz, DMSO-$d_6$, TMS): 2.22, s, 3H; 2.29, s, 3H; 3.57, s, 2H; 7.08, s, 1H; 7.68, s, 1H; 9.11, s, 1H; 12, 10, s, broad, 1H.

4. Ethyl 2-(6-hydroxy-5,7-dimethyl-1-benzofuran-3-yl)acetate

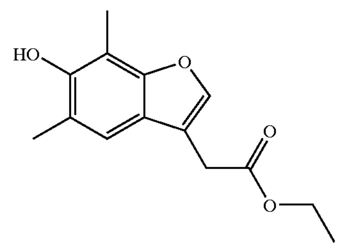

3.1 g (14 mmol) of 2-(6-hydroxy-5,7-dimethyl-1-benzofuran-3-yl) acetic acid are heated at reflux overnight in 1.72 ml of conc. sulfuric acid in 861 ml of ethanol. The mixture is concentrated down to 50 ml and then diluted with water and ethyl acetate; the phases are separated and the aqueous phase is extracted with ethyl acetate. The combined phases are washed with a saturated solution of NaCl, dried over sodium sulfate and concentrated. Chromatographic purification (dichloromethane) yields 2.6 g (75%) of ethyl 2-(6-hydroxy-5,7-dimethyl-1-benzofuran-3-yl)acetate.

$^1$H-NMR (300 MHz, DMSO-$d_6$, TMS): 1.19, t, 3H; 2.22, s, 3H; 2.29, s, 3H; 3.68, s, 2H; 4.10, quart. 2H; 7.09, s, 1H; 7.70, s, 1H; 8.38, s, 1H.

5. Ethyl 5-methoxybenzofuran-2-carboxylate

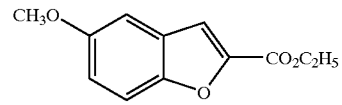

30.19 g (198.4 mmol) of 2-hydroxy-5-methoxy-benzaldehyde are dissolved in 300 ml of anhydrous N,N-dimethylformamide, after which 67.19 g (486.1 mmol) of potassium carbonate and 33.14 g (198.4 mmol) of ethyl 2-bromoactate are added and the mixture is stirred for 3 hours at an internal temperature of 80° C. The reaction mixture is cooled down and poured into 31 of ice water. The precipitate which accrues is filtered off with suction, washed with water and dried under high vacuum and over Sicapent for 18 hours; yield: 25.17 g (57%).

$R_f$=0.40 (dichloromethane). MS (DCI, $NH_3$): m/z=238 (100%, $[M+NH_4]^+$), 221 (5%, $[M+H]^+$). $^1$H-NMR (300 MHz, DMSO-$d_6$, TMS): 1.42, t, 3H; 3.86, s, 3H; 4.45, quart, 2H; 7.08, m, 2H; 7.48, m, 2h.

6. Ethyl 5-hydroxy-benzofuran-2-carboxylate and 5-hydroxy-benzofuran-2-carboxylic acid

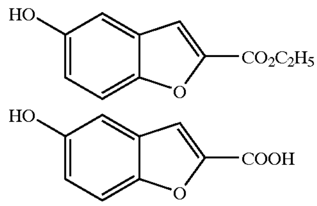

24.98 g (113,4 mmol) of ethyl 5-methoxy-benzofuran-2-carboxylate are dissolved in 500 ml of dichloromethane and the solution is cooled down to −78° C.; 28.42 g (113.4 mmol) of boron tribromide are then slowly added. The reaction mixture is warmed to 23° C. over approx. 2 hours and then subsequently stirred at this temperature for 20 hours; after that, it is mixed with 21 of dichloromethane and 21 of buffer solution (pH=7). The precipitate (fraction 1) which accrued in connection with this is filtered off with suction, washed with water and dichloromethane and dried under high vacuum (4.04 g). The solution phases are separated and the organic phase is subsequently extracted with the abovementioned buffer, dried using sodium sulfate and evaporated; the residue is then freed from the residual solvent under high vacuum (fraction 2, 11.82 g). The combined aqueous phases are extracted with ethyl acetate and the combined ester phases which are thus obtained are dried with sodium sulfate and evaporated; the residue is then freed from residual solvent under high vacuum (fraction 3, 5.84 g).

Fractions 1 and 3 are 5-hydroxybenzofuran-2-carboxylic acid.

$R_f$=0 (dichloromethane:methanol=100:1). MS (EI positive): m/z=178 (100%, $M^+$), 161 (21%, $[M-OH]^+$).

Fraction 2 is ethyl 5-hydroxybenzofuran-2-carboxylate.

$R_f$=0.11 (dichloromethane:methanol=100:1). $^1$H-NMR (300 MHz, $d_6$-DMSO, TMS): 1.33,t, 3H; 4.34, quart, 3H.

7. Ethyl 4,6-dibromo-5-hydroxybenzofuran-2-carboxylate and ethyl 5-acetoxy-4,6-dibromobenzofuran-2-carboxylate

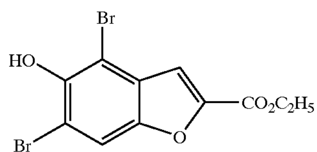

-continued

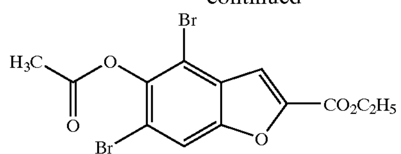

13.53 g (65,6 mmol) of ethyl 5-hydroxybenzofuran-2-carboxylate are dissolved in 200 ml of glacial acetic acid, after which a solution of 21 g (131.4 mmol) of bromine in 50 ml of glacial acetic acid is added dropwise and the mixture is stirred at 50° C. for 19 hours. 10.5 g (65.7 mmol) of bromine in 25 ml of glacial acetic acid are added to the incompletely reacted reaction mixture and the whole is stirred at 50° C. for a further 21 hours. After the mixture has been cooled down to room temperature, approx. 24 ml of a 39% solution of sodium bisulfate are added in order to destroy the excess bromine. The reaction mixture is stirred into 2.51 of ice water and the whole is extracted with ethyl acetate. The combined organic phases are washed consecutively with water, with buffer solution at pH=7 and with a saturated solution of sodium chloride, after which they are dried in sodium sulfate and evaporated. The resulting crude product is purified chromatographically (silica gel 60, Merck, cyclohexane:ethyl acetate=40:1 to 10:1); fraction 1 (2.13 g/8%) and fraction 2 (16.53 g/69%) accrue.

Fraction 1 is ethyl 5-acetoxy-4,6-dibromobenzofuran-2-carboxylate.

$R_f$=0.28 (cyclohexane:ethyl acetate=10:1). MS (DCI, $NH_3$): m/z=422/424/426 (52%/100%/50%, $[M+NH4]^+$).

Fraction 2 is ethyl 4,6-dibromo-5-hydroxybenzofuran-2-carboxylate.

$R_f$=0.20 (cyclohexane:ethyl acetate=10:1). MS (EI positive): m/z=362/364/366 (46%/100%/45%, $M^+$), 334/336/338 (23%/47%/22%, $[M-CO]^+$), 317/319/321 (13%/27%/13%, $[M-OC_2H_5]^+$).

8. Ethyl 6-methoxybenzofuran-2-carboxylate

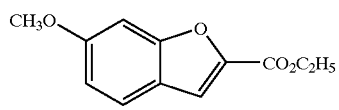

50.39 g (331.2 mmol) of 2-hydroxy-4-methoxybenzaldehyde are dissolved in 500 ml of anhydrous N,N-dimethylformamide, after which 112.14 g (811.4 mmol) of potassium carbonate and 55.31 g (331.2 mmol) of ethyl 2-bromoacetate are added and the mixture is stirred for 2 hours at an internal temperature of 80° C. The cooled suspension is stirred into 4.51 of ice water and, after subsequently stirring for 10 minutes, the resulting precipitate is filtered off with suction, washed with water and dried over Sicapent under high vacuum; yield 22.01 g (batch 1).

A further 23.64 g of crude product (batch 2) can be obtained after the aqueous phase has been acidified with concentrated hydrochloric acid and extracted with diethyl ether and ethyl acetate, the combined organic phases have been dried with sodium sulfate and the solvents have been evaporated off.

The following investigations and syntheses were carried out using batch 1 as the starting material.

$R_f$=0.24 (dichloromethane). MS (DCI, $NH_3$): m/z=238 (100%, $[M+NH_4]^+$), 221 (6%, $[M+H]^+$).

9. Ethyl 5,7-dibromo-6-methoxy-1-benzofuran-2-carboxylate

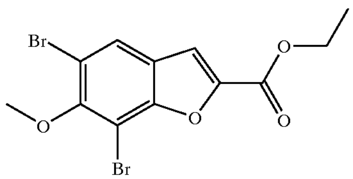

16 g (51,6 mmol) of 3,5-dibromo-2-hydroxy-4-methoxybenzaldehyde (Biorg. Med. Chem. 1998, 6, 1153–1162) and 17.84 g (129 mmol) of potassium carbonate are initially introduced in DMF and 8.62 g (51.6 mmol) of ethyl bromoacetate are then added dropwise to the mixture. The latter is stirred at 80° C. for 6 hours and then poured onto ice water after having been cooled; the precipitate is filtered off with suction. The precipitate is washed with water and dried. 15.47 g (79%) of ethyl 5,7-dibromo-6-methoxy-1-benzofuran-2-carboxylate are obtained.

$^{1}$H-NMR (200 MHz, $CDCl_3$, TMS): 1.43, t, 3H; 3.98, s, 3H; 4.46, quart, 2H; 7.50, s, 1H; 7.84, s, 1H.

10. 5,7-Dibromo-6-methoxy-1-benzofuran-2-carboxylic acid

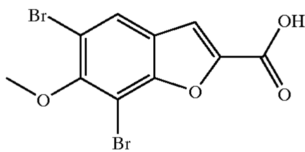

15.50 g (41 mmol) of 5,7-dibromo-6-methoxy-1-benzofuran-2-carboxylic acid are boiled, together with 79 ml of 1 N NaOH and refluxed for 2 hours in 318 ml of ethanol. The solid which has precipitated out is filtered off and dissolved in 1 N HCl and ethyl acetate. The organic phase is dried over magnesium sulfate and subjected to rotary evaporation. 9.12 g (65%) of 5,7-dibromo-6-methoxy-1-benzofuran-2-carboxylic acid are obtained.

$^{1}$H-NMR (200 MHz, DMSO-$d_6$, TMS): 3.83, s, 3H; 6.96, s, 1H; 7.92, s, 1H.

11. Methyl 4,6-dibromo-5-hydroxy-2-methyl-1-benzofuran-3-carboxylate

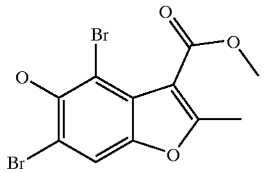

4.8 mmol of methyl 5-hydroxy-2-methyl-1-benzofuran-3-carboxylate are dissolved in 13.1 mmol of glacial acetic acid and 2 equivalents of $Br_2$ are added dropwise to this solution. The mixture is stirred at 50° C. for 3 hours, allowed to cool and then poured onto ice water. The resulting mixture is extracted twice with ethyl acetate, after which the organic phase is dried and the solvent is removed in vacuo. Crystallization yields 1.9 g (40%) of methyl 4,6-dibromo-5-hydroxy-2-methyl-1-benzofuran-3-carboxylate $R_f$(dichloromethane)=0.67

12. Ethyl 4,6-dibromo-2-(2-ethoxy-2-oxoethyl)-5-hydroxy-1-benzofuran-3-carboxylate

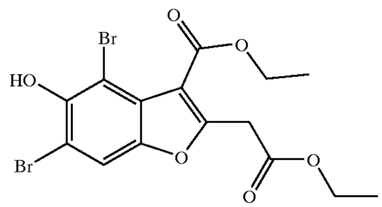

In analogy with example 11, 1.44 g (48%) of ethyl 4,6-dibromo-2-(2-ethoxy-2-oxoethyl)-5-hydroxy-1-benzofuran-3-carboxylate are obtained when using 3 of ethyl 2-(2-ethoxy-2-oxoethyl)-5-hydroxy-1-benzofuran-3-carboxylate as the starting material.

$R_f$(dichloromethane)=0.60

13. Ethyl (5-hydroxy-4,6-dimethyl-2,3-dihydro-1-benzofuran-2-yl)acetate

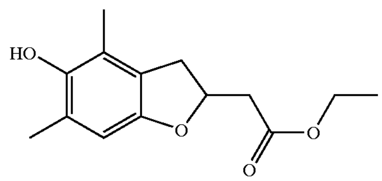

5.2 g of (5-hydroxy-4,6-dimethyl-2,3-dihydro-1-benzofuran-2-yl)acetic acid (J. Hetreocyclic Chem., 1993, 30, 679–690) are heated, at reflux for 6 hours, in 50 ml of ethanol and 2 ml of conc. sulfuric acid. The solvent is removed in vacuo and the residue is taken up in ethyl acetate; the organic phase is washed with a sat. solution of NaCl. Filtration takes places through silica gel, the solvent is removed in vacuo and crystallization takes place from heptane/ethyl (1:1). 320 mg (5.5%) of ethyl. (5-hydroxy-4,6-dimethyl-2,3-dihydro-1-benzofuran-2-yl)acetate are obtained.

$R_f$(dichloromethane)=0.21

14. Ethyl 4,6-dibromo-5-(3-isopropyl-4-methoxyphenoxy) benzofuran-2-carboxylate

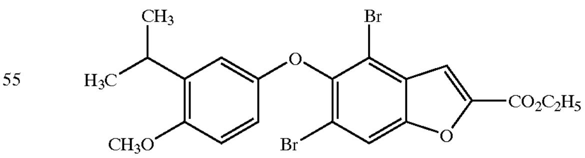

A solution of 5.00 g (13.7 mmol) of ethyl 4,6-dibromo-5-hydroxybenzofuran-2-carboxylate and 1.53 g (15.1 mmol) of triethylamine in 50 ml of dichloromethane is added dropwise, at 0° C. and while stirring and under an argon atmosphere, to 10.55 g (20.6 mmol) of bis-(3-isopropyl-4-methoxyphenyl)iodonium tetrafluoroborate (Synthesis: N. Yokoyama, G. N. Walker and A. J. Main, EP 580 550, page 12f (1994); N. Yokoyama, G. N. Walker, A. J. Main, J. L.

Stanton, M. M. Morrissey, C. Boehm, A. Engle, A. D. Neubert, J. M. Wasvary, Z. F. Stephan and R. E. Steele, J. Med. Chem. 38, 695 (1995)), and 1.75 g of copper bronze in 50 ml of dichloromethane and the mixture is stirred at 24° C. for 16 hours. The reaction mixture is filtered with suction through kieselguhr, which is then washed with dichloromethane; the resulting filtrate is then evaporated. The crude product is purified chromatographically (silica gel 60, Merck, cyclohexane:ethyl acetate=100:1 to 40:1), yield:6.74 g (96%).

$R_f$=0.20 (cyclohexane:ethyl acetate=20:1). MS (ESI): m/z=569/571/573 (12%/24%/14%, $[M+H_4+CH_3CN]^+$), 552/554/556 (24%/48%/27%, $[M+H+CH_3CN]^+$), 528/530/532 (26%/50%/29%, $[M+NH_4]^+$), 511/513/515 (52%/100%/54%, $[M+H]^+$). $^1$H-NMR (200 MHz, DMSO-$d_6$, TMS): 1.12, d, 6H; 1.37, t, 3H; 3.22, hept, 1H; 4.40, quart, 2H; 6.40,dd, 1H; 6.82, m, 2H; 7.67, s, 1H; 8.40, s, 1H.

15. Ethyl 4,6-dibromo-5-(4-hydroxy-3-isopropylphenoxy) benzofuran-2-carboxylate and 4,6-dibromo-5-(4-hydroxy-3-isopropylphenoxy)benzofuran-2-carboxylic acid

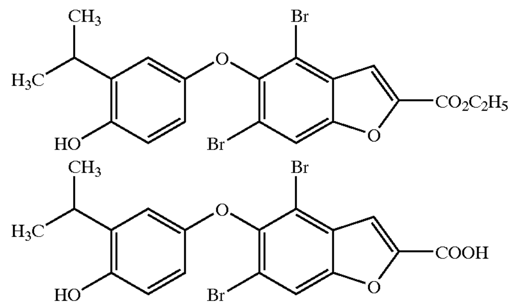

6.00 g (11.7 mmol) of ethyl 4,6-dibromo-5-(3-isopropyl-4-methoxyphenoxy)-benzofuran-2-carboxylate are dissolved in 120 ml of dichloromethane and 2.93 g (11.7 mmol) of boron tribromide are added dropwise, at −78° C. and under an argon atmosphere, to this solution. The reaction mixture is warmed to 24° C. over a period of approx. 30 minutes, then stirred at this temperature for 3 hours and, after that, stirred into 300 ml of ice water. The organic phase is washed several times with water and the combined aqueous phases are extracted with dichloromethane. The combined organic phases are washed with a saturated solution of sodium chloride and, after that, dried using solid sodium sulfate. After the solvent has been evaporated off, the product mixture is fractionated chromatographically (silica gel 60, Merck, dichloromethane to dichloromethane:methanol=5:1); fraction 1 (4.96 g) and fraction 2 (0.66 g) accrue.

Fraction 1 proves to be ethyl 4,6-dibromo-5-(4-hydroxy-3-isopropylphenoxy)benzo-furan-2-carboxylate.

$R_f$=0.85 (dichloromethane:methanol=20:1). MS (ESI): m/z=555/557/559 (11%/25%/12%, $[M+NH_4+CH_3CN]^+$), 538/540/542 (32%/58%/28%, $[M+H+CH_3CN]^+$),514/516/518 (40%/74%/39%, $[M+NH_4]^+$), 497/499/501 (51%/100%/49%, $[M+H]^+$). $^1$H-NMR (200 MHz, $d_6$-DMSO, TMS): 1.11, d, 6H; 1.35, t, 3H; 3.15, hept, 1H; 4.49, quart, 2H; 6.21, dd, 1H; 6.65, m, 2H; 7.63, s, 2H; 8.36 s, 1H; 9.06, s, 1H.

Fraction 2 proves to be 4,6-dibromo-5-(4-hydroxy-3-isopropylphenoxy)benzofuran-2-carboxylic acid.

$R_f$=0.06 (dichloromethane:methanol=20:1). MS (EI positive): m/z=468/470/472 (50%/100%/50%, $M^+$), 453/455/457 (20%/37%/18%, $[M-CH_3]^+$), 424/426/428 (5%/9%/4%, $[M-CO_2]^+$). $^1$H-NMR (200 MHz, $d_6$-DMSO, TMS): 1.11, d, 6H; 3.15, hept, 1H; 6.21, dd, 1H; 6.63, m, 2H; 6.92, s, 1H; 8.08, s, 1H; 9.09, s, 1H.

16. 4,6-Dibromo-5-(3-isopropyl-4-methoxyphenoxy)benzofuran-2-carboxylic acid

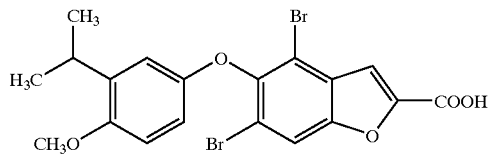

0.50 g (0.98 mmol) of ethyl 4,6-dibromo-5-(3-isopropyl-4-methoxyphenoxy)-benzofuran-2-carboxylate is dissolved in 8 ml of ethanol, after which 8 ml of 1M sodium hydroxide solution are added and the mixture is stirred at 24° C. for 1 hour. The reaction solution is adjusted to a Ph of 6 with 1M hydrochloric acid and poured into 250 ml of a buffer solution at pH=7; this mixture is then extracted with dichloromethane; yield: 0.40 g (85%).

$R_f$=0.1 (dichloromethane:methanol=20:1). MS (ESI): m/z=482/484/486 (50%/100%/52%, $M^+$).

17. 5-(4-Hydroxy-3-isopropylphenoxy)-4,6-dimethyl-1-benzofuran-2-carboxylic acid

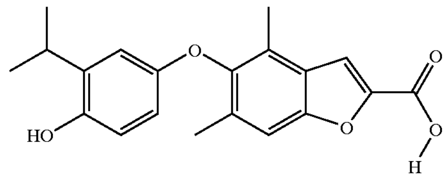

In analogy with WO 99/00 353, 30 mg (46%) of 5-(4-hydroxy-3-isopropylphenoxy)-4,6-dimethyl-1-benzofuran-2-carboxylic acid are obtained when using 90 mg of 4,6-dibromo-5-(3-isopropyl-4-hydroxyphenoxy)benzofuran-2-carboxylic acid and 40 equivalents of trimethyl stannane.

$^1$H-NMR (200 MHz, $d_6$-DMSO, TMS): 1.10, d, 6H; 2.13, s, 3H; 2.19, s, 3H; 3.16, sept, 1H; 6.18, dd, 21; 6.60, m, 2H; 7.07, s, 1H; 7.30, s, 1H; 8.90, s, 1H.

18. Ethyl 2-[6-(3-isopropyl-4-methoxyphenoxy)-5,7-dimethyl-1-benzofuran-3-yl]acetate

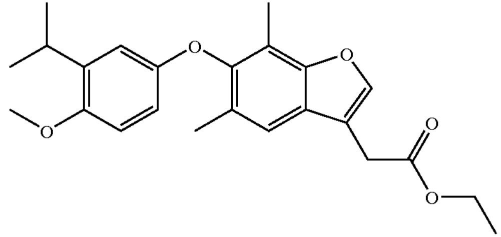

A solution of 60 mg (0.24 mmol) of ethyl 2-(6-hydroxy-5,7-dimethyl-1-benzofuran-3-yl)acetate and 27 mg (0.27 mmol) of triethylamine in 20 ml of dichloromethane is added dropwise, at 0° C. and in a darkened flask, to 185 mg (0.36 mmol) of bis(3-isopropyl-4-methoxyphenyl)iodonium tetrafluoroborate and 32 mg (0.48 mmol) of copper bronze in 20 ml of dichloromethane. The reaction mixture is stirred overnight at room temperature. Chromatographic purification of the reaction mixture yields 40 mg (42%) of ethyl 2-[6-(3-isopropyl-4-methoxyphenoxy)-5,7-dimethyl-1-benzofuran-3-yl]acetate.

$^1$H-NMR (200 MHz, DMSO-d$_6$, TMS): 1.11, d, 6H; 1.21, t, 3H; 2.13, s, 3H; 2.20, s, 3H; 3.20, hept, 1H; 3.71, s, 3H; 3.78, s, 2H; 4.14, qurt, 2H; 6.31, dd, 1H; 6.79, m, 2H; 7.36, s, 1H; 7.91, s, 1H.

19. Ethyl 2-[6-(4-hydroxy-3-isopropylphenoxy)-5,7-dimethyl-1-benzofuran-3-yl]-acetate

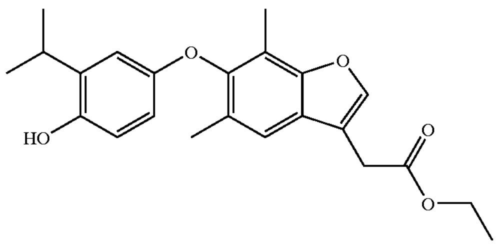

34 mg (0.09 mmol) of ethyl 2-[6-(3-isopropyl-4-methoxyphenoxy)-5,7-dimethyl-1-benzofuran-3-yl]acetate in 3 ml of dichloromethane are added, at 0° C., to 34 mg (0.26 mmol) of aluminum trichloride and 83 mg (1.3 mmol) of ethanethiol. The mixture is stirred at room temperature for 6 hours, concentrated in vacuo and purified chromatographically (toluene/ethyl acetate). 24 mg (73%) of ethyl 2-[6-(4-hydroxy-3-isopropylphenoxy)-5,7-dimethyl-1-benzofuran-3-yl]acetate are obtained.

$^1$H-NMR (200 MHz, DMSO-d$_6$, TMS): 1.11, d, 6H; 1.21, t, 3H; 2.12, s, 3H; 2.20, s, 3H; 3.17, hept, 1H; 3.76, s, 2H; 4.13, qurt, 2H; 6.21, dd, 1H; 6.65, m, 2H; 7.31, s, 1H; 7.90, s, 1H; 8.91, s, 1H.

20. [6-(4-Hydroxy-3-isopropylphenoxy)-5,7-dimethyl-1-benzofuran-3-yl]acetic acid

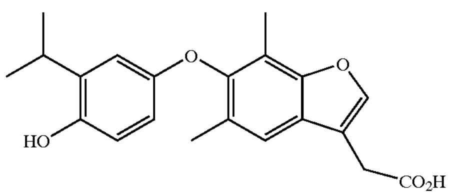

12 mg (72%) of [6-(4-hydroxy-3-isopropylphenoxy)-5,7-dimethyl-1-benzofuran-3-yl]acetic acid are obtained by subjecting 18 mg of ethyl 2-[6-(4-hydroxy-3-isopropylphenoxy)-5,7-dimethyl-1-benzofuran-3-yl]acetate to alkaline hydrolysis.

$^1$H-NMR (200 MHz, DMSO-d$_6$, TMS): 1.10, d, 6H; 2.12, s, 3H; 2.18, s, 3H; 3.12, sept, 1H; 3.66, s, 2H; 6.19, dd, 1H; 6.61, d, 1H; 6.68, d, 1H; 7.31, s, 1H; 7.88, s, 1H; 8.92, s, broad, 1H; 12.50, s, broad, 1H.

21. Ethyl 2-[6-(4-methoxyphenoxy)-5,7-dimethyl-1-benzofuran-3-yl]acetate

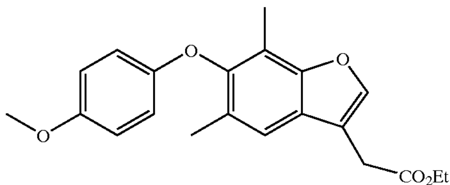

3.92 g (9.15 mmol) of bis(4-methoxyphenyl)iodonium tetrafluoroborate are initially introduced, together with 0.77 g of copper bronze, in 60 ml of dichloromethane. A solution of 1.50 g (6.04 mmol) of ethyl 2-(6-hydroxy-5,7-dimethyl-1-benzofuran-3-yl)acetate and 0.68 g of triethylamine in 40 ml of dichloromethane is added dropwise at 0° C. The reaction mixture is stirred overnight at room temperature. The solvent is removed in vacuo and the residue is subjected to chromatographic purification (cyclohexane/ethyl acetate=6:1). 0.76 g (23%) of ethyl 2-[6-(4-methoxyphenoxy)-5,7-dimethyl-1-benzofuran-3-yl]acetate is obtained.

$^1$H-NMR (300 MHz, CDCl$_3$, TMS): 1.27, t, 3H; 2.36, s, 3H; 2.42, s, 3H; 3.76, s, 2H; 3.87, s, 3H; 4.20, quart, 2H, 4.63, s, 1H; 7.00, d, 2H; 7.18, s, 1H; 7.78, d, 2H.

22. Ethyl 2-[6-(4-hydroxyphenoxy)-5,7-dimethyl-1-benzofuran-3-yl]acetate

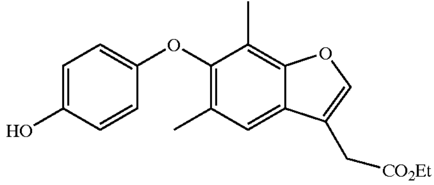

0.74 g (2.09 mmol) of ethyl 2-[6-(4-methoxyphenoxy)-5,7-dimethyl-1-benzofuran-3-yl]acetate, dissolved in 1 ml of dichloromethane, is [lacuna], at 0° C., to a solution of 0.84 g (6.26 mmol) of aluminum chloride and 0.65 g (10.44 mmol) of ethanethiol in 10 ml of dichloromethane. The reaction mixture is stirred overnight at room temperature, after which the solvent is removed in vacuo and the residue is subjected to chromatographic purification (cyclohexane/ethyl acetate=5.1). 0.52 g (73%) of ethyl 2-[6-(4-hydroxyphenoxy)-5,7-dimethyl-1-benzofuran-3-yl]acetate is obtained.

$^1$-NMR (300 MHz, CDCl$_3$, TMS): 1.26, t, 3H; 2.35, s, 3H; 2.43, s, 3H; 3.76, s, 2H; 4.21, quart., 2H; 4.64, s, 1H; 4.97, s, 1H; 6.93, d, 2H; 7.17, s, 1H; 7.71, d, 1H.

23. Methyl 4,6-dibromo-5-(3-isopropyl-4-methoxyphenoxy)-2-methyl-1-benzo-furan-3-carboxylate

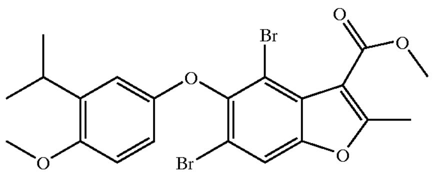

In analogy, 1.3 g of methyl 4,6-dibromo-5-(3-isopropyl-4-methoxyphenoxy)-2-methyl-1-benzofuran-3-carboxylate are obtained by reacting 1 g of methyl-4,6-dibromo- 5-hydroxy-2-methyl-1-benzofuran-3-carboxylate with bis-(3-isopropyl-4-methoxyphenyl)iodonium-tetrafluoroborate $R_f$=0.75 (toluene)

24. Methyl 4,6-dibromo-5-(4-hydroxy-3-isopropylphenoxy)-2-methyl-1-benzofuran-3-carboxylate

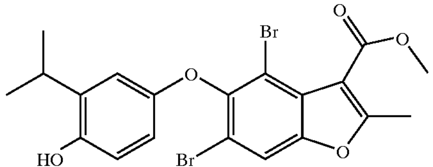

In analogy, methyl 4,6-dibromo-5-(4-hydroxy-3-isopropylphenoxy)-2-methyl-1-benzofuran-3-carboxylate is obtained by reacting methyl 4,6-dibromo-5-(3-isopropyl-4-methoxyphenoxy)-2-methyl-1-benzofuran-3-carboxylate with $AlCl_3$/ethanethiol.

$R_f$(toluene)=0.21

25. 4,6-Dibromo-5-(4-hydroxy-3-isopropylphenoxy)-2-methyl-1-benzofuran-3-carboxylic acid

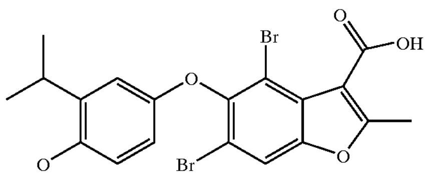

In analogy, 4,6-Dibromo-5-(4-hydroxy-3-isopropylphenoxy)-2-methyl-1-benzofuran-3-carboxylic acid is obtained by reacting methyl 4,6-dibromo-5-(3-isopropyl-4-methoxyphenoxy)-2-methyl-1-benzofuran-3-carboxylate with 2 equivalents of $BBr_3$.

$R_f$=0.31 (dichloromethane/methanol=95/5)

26. Ethyl 4,6-dibromo-2-(2-ethoxy-2-oxoethyl)-5-(3-isopropyl-4-methoxyphenoxy)-1-benzofuran-3-carboxylate

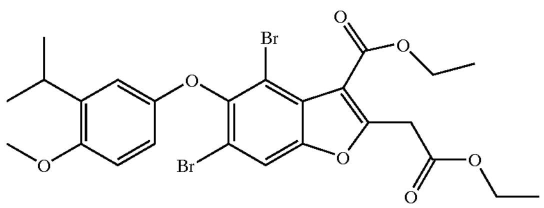

In analogy with example, 0.38 g (57%) of ethyl 4,6-dibromo-2-(2-ethoxy-2-oxoethyl)-5-(3-isopropyl-4-methoxyphenoxy)-1-benzofuran-3-carboxylate is obtained by reacting 0.5 g of ethyl 4,6-dibromo-2-(2-ethoxy-2-oxoethyl)-5-hydroxy-1-benzofuran-3-carboxylate with bis(3-isopropyl-4-methoxyphenyl)iodonium tetra-fluoroborate.

$R_f$=0.15 (toluene)

27. Ethyl [5-(3-isopropyl-4-methoxyphenoxy)-4,6-dimethyl-2,3-dihydro-1-benzofuran-2-yl]acetate

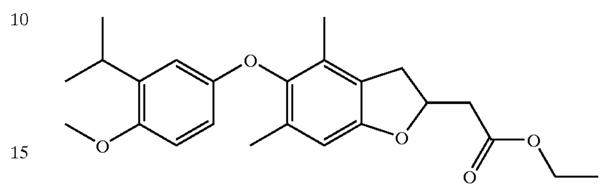

In analogy, 83 mg (17%) of ethyl [5-(3-isopropyl-4-methoxyphenoxy)-4,6-dimethyl-2,3-dihydro-1-benzofuran-2-yl]acetate are obtained using 300 mg of ethyl (5-hydroxy-4,6-dimethyl-2,3-dihydro -1-benzofuran-2-yl)acetate and bis(3-isopropyl-4-methoxyphenyl)iodonium tetra-fluoroborate as the starting compounds.

$R_f$=0.68 (toluerie/ethyl acetate=4/1)

28. Ethyl [5-(4-hydroxy-3-isopropylphenoxy)-4,6-dimethyl-2,3-dihydro-1-benzofuran-2-yl]acetate

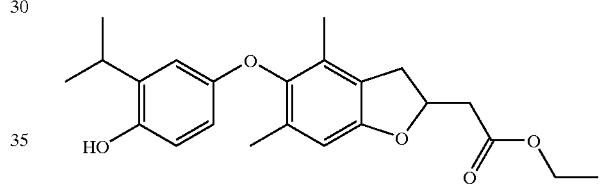

In analogy, 39 mg (49%) of ethyl [5-(4-hydroxy-3-isopropylphenoxy)-4,6-dimethyl-2,3-dihydro-1-benzofuran-2-yl]acetate are obtained by reacting 83 mg of ethyl [5-(3-isopropyl-4-methoxyphenoxy)-4,6-dimethyl-2,3-dihydro-1-benzofuran-2-yl]acetate with $AlCl_3$/ethanethiol.

$R_f$=0.53(toluene/ethyl acetate=4/1)

29. [5-(4-Hydroxy-3-isopropylphenoxy)-4,6-dimethyl-2,3-dihydro-1-benzofuran-2-yl]acetatic acid

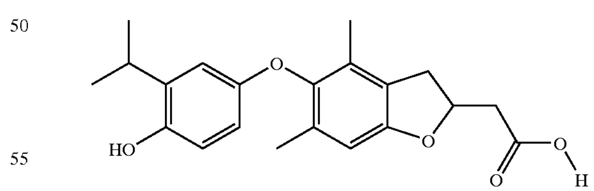

Alkaline hydrolysis (1 N NaOH) of 40 mg of ethyl [5-(4-hydroxy-3-isopropyl-phenoxy)-4,6-dimethyl-2,3-dihydro-1-benzofuran-2-yl]acetate yields 7.5 mg (20%) of [5-(4-hydroxy-3-isopropylphenoxy)-4,6-dimethyl-2,3-dihydro-1-benzofuran-2-yl]acetic acid.

$^1$H-NMR (400 MHz, DMSO-$d_6$, TMS):1.1.0, d, 6H; 1.92, s, 3H; 1.97, s, 3H; 2.70, m, 2H; 2.81, m, 1H; 3.13, sept, 1H; 3.28, m, 2H; 5.08, m, 1H; 6.17, dd, 1H; 6.50, s, 1H; 6.61, d, 1H; 6.64, d, 1H; 8.82, s, 1H; 12.39, s, broad, 1H.

30. Ethyl 4,6-dibromo-5-(4-methoxyphenoxy)-1-benzofuran-2-carboxylate

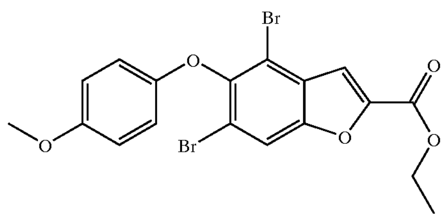

In analogy with THL 1998, 39, 2937–2940, ethyl 4,6-dibromo-5-(4-methoxyphenoxy)-1-benzofuran-2-carboxylate is obtained in 48% yield by reacting 1 mmol of ethyl 4,6-dibromo-5-hydroxy-benzofuran-2-carboxylate with 3 mmol [lacuna].

$R_f$=0.82(toluene/ethyl acetate=4:1)

31. Ethyl 4,6-dibromo-5-[3-(4-fluorobenzoyl)-4-methoxyphenoxy]-1-benzofuran-2-carboxylate

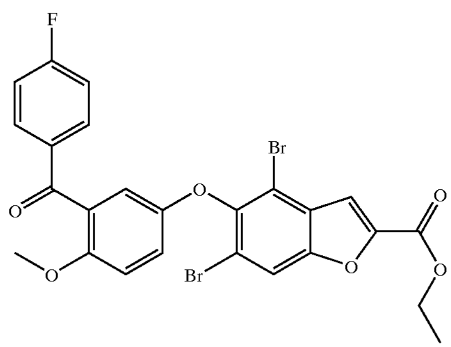

In analogy with J. Med. Chem. 1995, 38, 695–707, ethyl 4,6-dibromo-5-[3-(4-fluorobenzoyl)-4-methoxyphenoxy]-1-benzofuran-2-carboxylate is obtained in 64% yield by the Friedel-Crafts acylation of ethyl 4,6-dibromo-5-(4-methoxyphenoxy)-1-benzofuran-2-carboxylate.

$R_f$=0.66(toluene/ethyl acetate=9:1

32. Ethyl 4,6-dibromo-5-[3-(4-fluorobenzoyl)-4-hydroxyphenoxy]-1-benzofuran-2-carboxylate

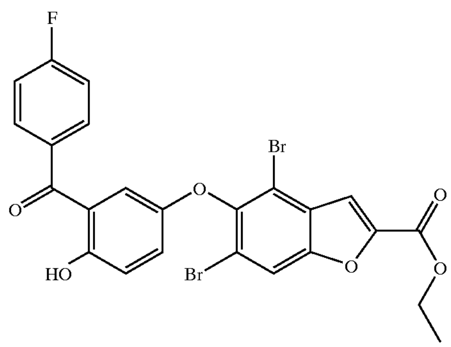

Ether cleavage of 108 mg of ethyl 4,6-dibromo-5-[3-(4-fluorobenzoyl)-4-methoxyphenoxy]-1-benzofuran-2-carboxylate with $AlCl_3$/ethanethiol, in analogy with example . . . , yields 49 mg (47%) of ethyl 4,6-dibromo-5-[3-(4-fluorobenzoyl)-4-hydroxyphenoxy]-1-benzofuran-2-carboxylate.

$R_f$=0.81 (toluene/ethyl acetate=9:1)

33. 4.6-Dibromo-5-[3-(4-fluorobenzoyl)-4-hydroxyphenoxy]-1-benzofuran-2-carboxylic acid

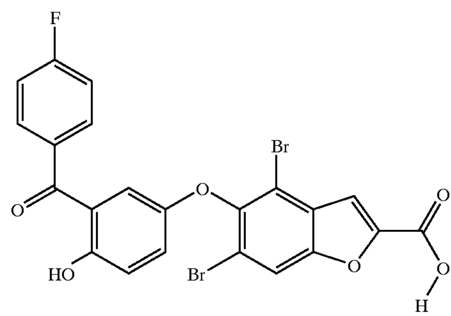

92 mg (84%) of 4,6-dibromo-5-[3-(4-fluorobenzoyl)-4-hydroxyphenoxy]-1-benzofuran-2-carboxylic acid are obtained by the alkaline hydrolysis of 115 mg of ethyl 4,6-dibromo-5-[3-(4-fluorobenzoyl)-4-hydroxyphenoxy]-1-benzofuran-2-carboxylate with 1 N NaOH.

$^1$H-NMR (400 MHz, DMSO-$d_6$, TMS):6.70, m, 1H; 6.95, m, 2H; 7.23, s, 1H; 7.35, m, 1H; 7.79, m, 1H; 8.22, s, 1H.

34. 4,6-Dibromo-5-{3-[(4-fluorophenyl)(hydroxy)methyl]-4-hydroxyphenoxy}-1-benzofuran-2-carboxylic acid

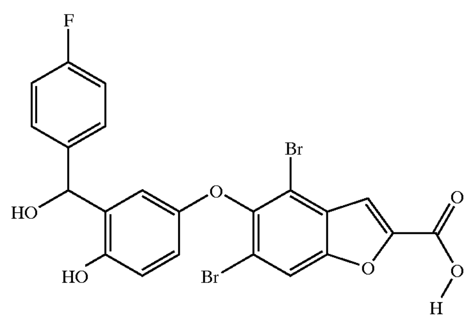

50 mg of 4,6-dibromo-5-[3-(4-fluorobenzoyl)-4-hydroxyphenoxy]-1-benzofuran-2-carboxylic acid are stirred, at 0° C. for 30 mins, with 1 equivalent of sodium borohydride in 10 ml of methanol. The reaction is terminated with 6.2 ml of 1 N HCl, after which the mixture is evaporated to dryness and the residue is purified chromatographically.

$^1$H-NMR (400 MHz, DMSO-$d_6$, TMS): 5.77, d, 1H; 5.89, d, 1H; 6.45, d, 1H; 6.68, d, 1H; 6.89–6.98, m, 2H; 7.09, m, 2H; 7.72m, 2H; 8.08, s, 1H; 9.20, s, 1H.

Application Example

In the T3 promoter assay cell tert., the compounds of examples 15, 17, 18, 28 and 32 exhibit an effect of 0.5–240 nm.

The invention claimed is:

1. Compounds of the general formula (I)

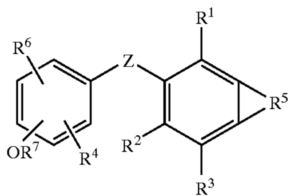

(I)

in which

Z is O, S, SO, $SO_2$, CHF or $CF_2$, $R^1$ and $R^2$ are identical or different and are hydrogen, halogen, cyano, $(C_1–C_6)$-alkyl, $CF_3$, $CHF_2$, $CH_2F$, vinyl or $(C_3–C_7)$-cycloalkyl, $R^3$ is hydrogen, halogen, cyano, $(C_1–C_6)$-alkyl or $CF_3$, $R^4$ is hydrogen, hydroxyl, halogen, cyano, nitro, $(C_1–C_4)$-alkyl or the radical of the formula $NR^9R^{10}$, where $R^9$ and $R^{10}$ are identical or different and are in each case hydrogen, phenyl, benzyl, $(C_1–C_6)$-alkyl or $(C_3–C_8)$-cycloalkyl, which, for their part, are optionally substituted, once or more than once, identically or differently, by halogen, hydroxyl, amino, carboxyl, $(C_1–C_4)$-alkoxy, $(C_1–C_4)$-alkoxycarbonyl, $(C_1–C_4)$-alkoxycarbonylamino, $(C_1–C_5)$-alkanoyloxy, or phenyl which is optionally substituted by halogen or hydroxyl, $R^5$ forms, together with the two carbon atoms of the phenyl ring, a saturated or unsaturated furan ring which is optionally substituted, once or twice, identically or differently, $R^6$ is hydrogen, cyano, halogen or a group of the formula $-M_a-R^{11}$ in which;

M is a carbonyl group, a sulfonyl group or a methylene group, a is the number 0 or 1 or, in the case where M is a methylene group, is a number 0, 1, 2 or 3, and $R^{11}$ is hydrogen, $OR^{15}$, $NR^{16}R^{17}$, $(C_1–C_{10})$-alkyl, $(C_3–C_8)$-cycloalkyl, $(C_2–C_6)$-alkenyl, $(C_6–C_{10})$-aryl, or $(C_6–C_{10})$-arylmethyl, where the abovementioned radicals are optionally substituted by one, two or three identical or different substituents selected from the group halogen, hydroxyl, oxo, cyano, nitro, amino, $NR^{18}R^{19}$, trifluoromethyl, $(C_1–C_6)$-alkyl, $(C_1–C_6)$-alkoxy which is optionally substituted by $R^{20}$, $(C_3–C_8)$-cycloalkyl, $(C_6–C_{10})$-aryl which is, for its part, optionally substituted by halogen, $(C_1–C_4)$-alkyl, $(C_1–C_4)$-alkoxy, trifluoromethyl, nitro or cyano, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH— C(O)—$OR^{28}$, where $R^{15}$ to $R^{28}$ have the meanings given for $R^9$ or $R^{10}$ and, independently of each other, are identical to or different from this substituent, $R^7$ is hydrogen cation alkyl or acctyl, and also their pharmaceutically tolerated salts, solvates, hydrates and hydrates of the salts.

2. Compounds of the general formula (I) as claimed in claim 1 in which

Z is O or S, $R^1$ and $R^2$ are identical or different and are halogen, fluorine, chlorine, bromine, $(C_1–C_4)$-alkyl, $CF_3$, $CHF_2$, $CH_2F$, vinyl or $(C_3–C_5)$-cycloalkyl, $R^3$ is hydrogen, fluorine, chlorine, bromine, $(C_1–C_4)$-alkyl or $CF_3$, $R^4$ is hydrogen, halogen or $(C_1–C_4)$-alkyl, $R^5$ forms, together with the two carbon atoms of the phenyl ring, a saturated or unsaturated furan ring which is optionally substituted, once or twice, identically or differently, $R^6$ is hydrogen, cyano, halogen or a group of the formula $-M_a-R^{11}$ in which M is a carbonyl group, a sulfonyl group or a methylene group, a is the number 0 or 1, and $R^{11}$ is hydrogen, hydroxyl, $(C_1–C_6)$-alkoxy, $NR^{16}R^{17}$, $(C_1–C_{10})$-alkyl, $(C_3–C_7)$-cycloalkyl, $(C_2–C_4)$-alkenyl, naphthyl, phenyl or benzyl, where the abovementioned radicals are optionally substituted by one, two or three identical or different substituents selected from the group halogen, hydroxyl, cyano, nitro, amino, $NR^{18}R^{19}$, trifluoromethyl, $(C_1–C_4)$-alkyl, $(C_1–C_4)$-alkoxy, $(C_3–C_7)$-cycloalkyl, phenyl which is, for its part, optionally substituted by halogen, $(C_1–C_4)$-alkyl, $(C_1–C_4)$-alkoxy, trifluoromethyl, nitro or cyano, —O—C(O)—$R^{21}$, —C(O)—$OR^{22}$, —C(O)—$NR^{23}R^{24}$, —$SO_2$—$NR^{25}$ $R^{26}$, —NH—C(O)—$R^{27}$ and —NH—C(O)—$OR^{28}$, where $R^{16}$, $R^{17}$, $R^{18}$, $R^{19}$, $R^{21}$, $R^{22}$, $R^{23}$, $R^{24}$, $R^{25}$, $R^{26}$, $R^{27}$ and $R^{28}$ are identical or different and are in each case hydrogen, phenyl, benzyl, $(C_1–C_6)$-alkyl or $(C_3–C_6)$-cycloalkyl which, for their part, are optionally substituted, once or more than once, identically or differently, by halogen, hydroxyl, amino, carboxyl, $(C_1–C_4)$-alkoxy, $(C_1–C_4)$-alkoxycarbonyl, $(C_1–C_4)$-alkoxycarbonylamino, $(C_1–C_5)$-alkanoyloxy, a heterocycle or phenyl which is optionally substituted by halogen or hydroxyl, $R^7$ is hydrogen, and their pharmaceutically tolerated salts, solvates and hydrates of the salts.

3. Compounds of the general formula (I) as claimed in claim 1, in which

Z is O, $R^1$ and $R^2$ are identical or different and are hydrogen, fluorine, chlorine, bromine, methyl, ethyl, n-, i- or s-propyl, n-, i-, s- or t-butyl, $CF_3$, $CHF_2$, $CH_2F$, vinyl or $(C_3–C_5)$-cycloalkyl, $R^3$ is hydrogen or methyl, $R^4$ is methyl, fluorine, chlorine or, in particular, hydrogen, $R^5$ forms, together with the two carbon atoms of the phenyl ring, a saturated or unsaturated furan ring which is optionally substituted, once or twice, identically or differently, $R^6$ is hydrogen, cyano, halogen or a group of the formula $-M_a-R^{11}$ in which M is a carbonyl group or a methylene group, a is the number 0 or 1, and $R^{11}$ is hydrogen, hydroxyl, $(C_1–C_4)$-alkyl, $(C_1–C_4)$-alkoxy, $NR^{18}R^{19}$, —CH(OH)—$R^{29}$, $(C_3–C_7)$-cycloalkyl, phenyl or benzyl, where the abovementioned radicals are optionally substituted by one or two identical or different substituents selected from the group fluorine, chlorine, bromine, hydroxyl, cyano, nitro, amino, $NR^{18}R^{19}$, trifluoromethyl, $(C_1–C_4)$-alkyl, $(C_1–C_4)$-alkoxy, $(C_3–C_7)$-cycloalkyl, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{18}$, $R^{19}$, $R^{21}$, $R^{22}$, $R^{23}$, $R^{24}$, $R^{25}$, $R^{26}$, $R^{27}$, $R^{28}$ and $R^{29}$ are identical or different and are in each case hydrogen, phenyl, benzyl, $(C_1–C_4)$-alkyl or $(C_3–C_6)$-cycloalkyl which, for their part, are optionally substituted, once or twice, identically or differently, by fluorine, chlorine, hydroxyl, amino, carboxyl, $(C_1–C_4)$-alkoxy, $(C_1–C_4)$-alkoxycarbonyl, $(C_1–C_4)$-alkoxycarbonyl-amino, $(C_1–C_5)$-akanoyloxy, a heterocycle or phenyl which is optionally substituted by fluorine, chlorine or hydroxyl, $R^7$ is hydrogen, and also their pharmaceutically tolerated salts, solvates and hydrates and hydrates of the salts.

4. Compounds of the general formula (I) as claimed in claim 1, in which

Z is O, $R^1$ and $R^2$ are identical or different and are hydrogen, bromine, chlorine, $CF_3$ or methyl with the proviso that at least one substituent is not hydrogen, $R^3$ is hydrogen or methyl, $R^4$ is hydrogen, $R^5$ forms, together with the two carbon atoms of the phenyl ring, a saturated or unsaturated furan ring which is optionally substituted, once or twice, identically or differently, $R^6$ is hydrogen, methyl, ethyl n- or i-propyl, n-, i-, s- or t-butyl, or is a carbonyl group or a group —CH(OH) which is substituted by phenyl which is optionally substituted by fluorine, chlorine, cyano, nitro, trifluoromethyl, methyl, methoxy, carboxyl or methoxycarbonyl, $R^7$ is hydrogen, and also their pharmaceutically tolerated salts, solvates and hydrates and hydrates of the salts.

5. Compounds of the general formula (I) as claimed in claim 1, in which, $R^5$ forms, together with the two carbon atoms of the phenyl ring, a group (Ib), (Ic) or (Id)

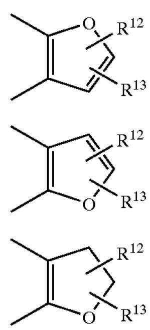

in which $R^{12}$ and $R^{13}$ are identical or different and are hydrogen, $(C_1–C_6)$alkyl, $(C_1–C_6)$-alkoxy, halogen, or are a group of the formula $—NR^{30}R^{31}$, in which $R^{30}$ and $R^{31}$ are identical or different and are hydrogen, $(C_1–C_6)$alkyl or $(C_3–C_8)$cycloalkyl which are optionally substituted by amino or $(C_1–C_6)$alkoxy, or are a group of the formula $$-A-(CH_2)_n—C(O)—R^{32}$$

in which

A is a bond, O, S or C(O), or is a straight-chain or branched alkylene group having from 1 to 6 carbon atoms which is optionally substituted by halogen, hydroxyl and/or amino, or is $NR^{33}$, in which $R^{33}$ is hydrogen, $(C_1–C_6)$alkyl or $(C_3–C_8)$cycloalkyl which are optionally substituted by amino or $(C_1–C_6)$ alkoxy, n is a number from 0 to 3

$R^{32}$ is hydroxyl, halogen or $(C_1–C_6)$alkyl or is a group $—NR^{30}R^{31}$ or is a group $—OR^{34}$ in which $R^{30}$, $R^{31}$ and $R^{34}$ have the abovementioned meaning of $R^{30}$ and $R^{31}$ and can be identical to or different from these latter.

6. Pharmaceutical composition comprising at least one compound of the general formula (I) as defined in claim 1 and auxiliary substances and carrier substances.

7. Process for producing medicaments, characterized in that at least one compound of the general formula (I), as defined in claim 1, is converted into a suitable form of administration using auxiliary substances and carrier substances.

8. A method of treating hypercholesterolemia, comprising administering to a patient in need thereof an effective amount of a compound of claim 1.

9. The method of claim 8, wherein the compound of claim 1 is used in combination with other pharmaceutically active compounds.

10. Process for preparing compounds of the general formula (I) as defined in claim 1, characterized in that reactive benzofuran derivatives of the general formula (II) are reacted with reactive phenyl derivatives of the general formula (III)

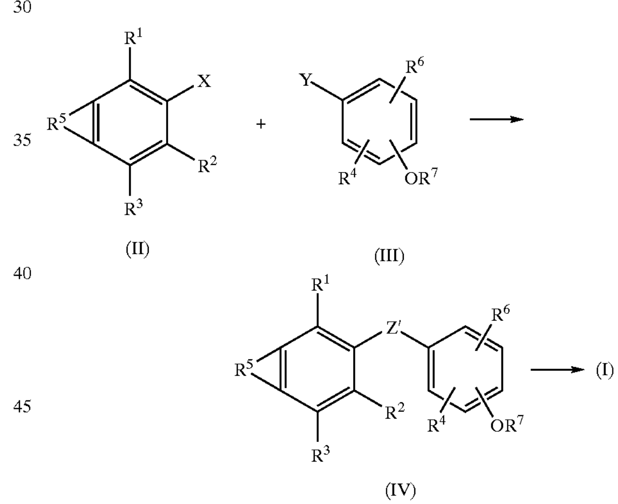

where the substituents $R^1$, $R^2$, $R^4$, $R^5$, $R^6$ and $R^7$ have the meanings given in claim 1, and X and Y are in each case groups of opposing reactivity, Z' has the meaning given for Z or is

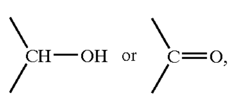

where appropriate in the presence of inert solvents and catalysts and where appropriate while isolating the intermediates of the general formula (IV), or directly to give compounds of the formula (I).

* * * * *